US006346540B1

(12) United States Patent
Janssens et al.

(10) Patent No.: US 6,346,540 B1

(45) Date of Patent: Feb. 12, 2002

(54) 1-(1,2-DISUBSTITUTED PIPEIDINYL)-4-SUBSTITUTED PIPERIDINE DERIVATIVES

(75) Inventors: Frans Eduard Janssens, Bonheiden; François Maria Sommen, Wortel; Dominique Louis Nestor Ghislaine Surleraux, Machelen; Yves Emiel Maria Van Roosbroeck, Heist-op den-Berg, all of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/615,523

(22) Filed: Jul. 13, 2000

Related U.S. Application Data

(63) Continuation of application No. 09/102,295, filed as application No. PCT/EP96/05883 on Dec. 20, 1996, now Pat. No. 6,169,097.

(30) Foreign Application Priority Data

Dec. 27, 1995 (EP) ........................................... 95203651

(51) Int. Cl.[7] ...................... A61K 31/454; A61K 31/55; C07D 401/04; C07D 403/04

(52) U.S. Cl. ...................... 514/326; 546/208; 540/597; 514/212

(58) Field of Search ......................... 546/208; 540/597; 514/212, 326

(56) References Cited

U.S. PATENT DOCUMENTS

| | | | |
|---|---|---|---|
| 5,541,195 A | 7/1996 | Schilling et al. | |
| 5,814,636 A | 9/1998 | Katano et al. | |
| 6,110,939 A * | 8/2000 | Janssens et al. | 514/322 |

FOREIGN PATENT DOCUMENTS

| | | |
|---|---|---|
| EP | 0 151 824 A2 | 8/1985 |
| WO | WO 93/14083 | 7/1993 |
| WO | WO 96/10562 | 4/1996 |
| WO | WO 97/16440 | 5/1997 |
| WO | WO 97/24324 | 7/1997 |

* cited by examiner

*Primary Examiner*—C. S. Aulakh

(74) *Attorney, Agent, or Firm*—Mary Appollina

(57) ABSTRACT

The present invention concerns compounds of formula (I)

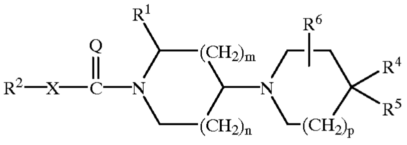

the N-oxide forms, the pharmaceutically acceptable addition salts and stereochemically isomeric forms thereof, wherein n is 0, 1 or 2; m is 1 or 2, provided that if m is 2, then n is 1; p is 0, 1 or 2; =Q is =O or $=NR_3$; X is a covalent bond or a bivalent radical of formula —O—, —S—, $—NR^3—$; $R^1$ is $Ar^1$; $Ar^1C_{1-6}$alkyl or di($Ar^1$)$C_{1-6}$alkyl, wherein each $C_{1-6}$alkyl group is optionally substituted with hydroxy, $C_{1-4}$alkyloxy, oxo or a ketalized oxo substituent of formula $—O—CH_2—CH_2—O—$ or $—O—CH_2—CH_2—CH_2—O—$; $R^2$ is $Ar^2$; $Ar^2C_{1-6}$alkyl; Het or Het$C_{1-6}$alkyl; $R^3$ is hydrogen or $C_{1-6}$alkyl; $R^4$ is hydrogen; $C_{1-4}$alkyl; $C_{1-4}$alkyloxy$C_{1-4}$alkyl; hydroxy$C_{1-4}$alkyl; carboxyl; $C_{1-4}$alkyloxycarbonyl or $Ar^3$; $R^5$ is hydrogen; hydroxy; $Ar^3$; $Ar^3C_{1-6}$alkyloxy; di($Ar^3$)$C_{1-6}$alkyloxy; $Ar^3C_{1-6}$alkylthio; di($Ar^3$)$C_{1-6}$alkylthio; $Ar^3C_{1-6}$alkylsulfoxy; di($Ar^3$)$C_{1-6}$ alkylsulfoxy; $Ar^3C_{1-6}$alkylsulfonyl; di($Ar^3$)$C_{1-6}$ alkylsulfonyl; $—NR^7R^8$; $C_{1-6}$alkyl substituted with $—NR^7R^8$; or a radical of formula (a-1) or (a-2); $R^4$ and $R^5$ may also be taken together; $R^6$ is hydroxy; $C_{1-6}$alkyloxy; $C_{1-6}$alkyl or $Ar^3C_{1-6}$alkyl; $Ar^1$, $Ar^2$ and $Ar^3$ are phenyl or substituted phenyl; $Ar^2$ is also naphtalenyl; and Het is an optionally substituted monocyclic or bicyclic heterocycle; as substance P antagonists; their preparation, compositions containing them and their use as a medicine.

8 Claims, No Drawings

1-(1,2-DISUBSTITUTED PIPEIDINYL)-4-SUBSTITUTED PIPERIDINE DERIVATIVES

This is a continuation of prior application No. 09/102,295, filed Jun. 22, 1998, now U.S. Pat. No. 6,169,097, which is the U.S. national stage of PCT/EP96/05883, filed Dec. 20, 1996.

This invention concerns 1-(1,2-disubstituted piperidinyl)-4-substituted piperidine derivatives having tachykinin antagonistic activity, in particular substance P antagonistic activity, and their preparation; it further relates to compositions comprising them, as well as their use as a medicine.

Substance P is a naturally occurring neuropeptide of the tachykinin family. There are ample studies showing that substance P and other tachykinins are involved in a variety of biological actions, and therefore, play an essential role in various disorders (Regoli et al., Pharmacological Reviews 46(4), 1994, p. 551–599, "Receptors and Antagonists for Substance P and Related Peptides"). The development of tachykinin antagonists has led to date to a series of peptide compounds of which might be anticipated that they are metabolically too labile to be employed as pharmaceutically active substances (Longmore J. et al., DN&P 8(1), February 1995, p. 5–23, "Neurokinin Receptors"). The present invention concerns nonpeptide tachykinin antagonists, in particular nonpeptide substance P antagonists, which in general are metabolically more stable, and hence, may be more appropriate as pharmaceutically active substances.

Several nonpeptide tachykinin antagonists are disclosed in the art. For instance, EP-0,532,456-A, published on Mar. 17, 1993, discloses 1-acylpiperidine compounds, in particular 2-arylalkyl-1-arylcarbonyl-4-piperidinamine derivatives, and their use as substance P antagonists.

EP-0,151,824-A and EP-0,151,826-A disclose structurally related 1-(1-(carbonyl or imino)-4-piperidinyl)-4-piperidinamine derivatives as histamine- and serotonine antagonists.

The present compounds differ from the art compounds by their structure and by their favourable pharmacological properties.

The present invention concerns compounds of formula (I)

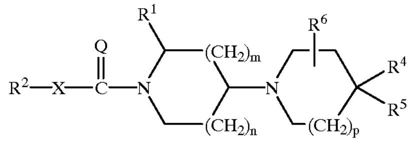

the N-oxide forms, the pharmaceutically acceptable acid or base addition salts and stereochemically isomeric forms thereof, wherein n is 0, 1 or 2;

m is 1 or 2, provided that if m is 2, then n is 1;

p is 0, 1 or 2;

=Q is =O or =$NR^3$;

X is a covalent bond or a bivalent radical of formula —O—, —S—, —$NR^3$—;

$R^1$ is $Ar^1$; $Ar^1C_{1-6}$alkyl or di($Ar^1$)$C_{1-6}$alkyl, wherein each $C_{1-6}$alkyl group is optionally substituted with hydroxy, $C_{1-4}$alkyloxy, oxo or a ketalized oxo substituent of formula —O—$CH_2$—$CH_2$—O— or —O—$CH_2$—$CH_2$—$CH_2$—O—;

$R^2$ is $Ar^2$; $Ar^2C_{1-6}$alkyl; Het or Het$C_{1-6}$alkyl;

$R^3$ is hydrogen or $C_{1-6}$alkyl;

$R^4$ is hydrogen; $C_{1-4}$alkyl; $C_{1-4}$alkyloxy$C_{1-4}$alkyl; hydroxy$C_{1-4}$alkyl; carboxyl; $C_{1-4}$alkyloxycarbonyl or $Ar^3$;

$R^5$ is hydrogen; hydroxy; $Ar^3$; $Ar^3C_{1-6}$alkyloxy; di($Ar^3$)$C_{1-6}$alkyloxy; $Ar^3C_{1-6}$alkylthio; di($Ar^3$)$C_{1-6}$alkylthio; $Ar^3C_{1-6}$ alkylsulfoxy; di($Ar^3$)$C_{1-6}$alkylsulfoxy; $Ar^3C_{1-6}$alkylsulfonyl; di($Ar^3$)$C_{1-6}$alkylsulfonyl; —$NR^7R^8$; $C_{1-6}$alkyl substituted with —$NR^7R^8$; or a radical of formula (a-1)

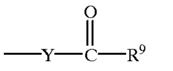

or (a-2)

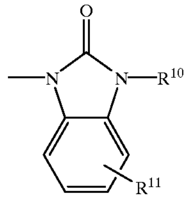

wherein $R^7$ is hydrogen; $C_{1-6}$alkyl; pyridinyl or $Ar^3$;

$R^8$ is hydrogen; $C_{1-6}$alkyl; $Ar^3C_{1-6}$alkyl; di($Ar^3$)$C_{1-6}$ alkyl; imidazolyl substituted with $Ar^3$, $C_{1-6}$alkyl or $Ar^3C_{1-6}$alkyl; benzoxazolyl or benzothiazolyl;

$R^9$ is hydrogen; hydroxy; $C_{1-6}$alkyl; $C_{1-6}$alkyloxy; $Ar^3$; $Ar^3C_{1-6}$alkyl; di($Ar^3$)-$C_{1-6}$alkyl; amino; mono- or di($C_{1-6}$alkyl)amino; imidazolyl; imidazolyl substituted with $Ar^3$, $C_{1-6}$alkyl or $Ar^3C_{1-6}$alkyl; pyrrolidinyl; piperidinyl; homopiperidinyl; morpholinyl or thiomorpholinyl;

$R^{10}$ is hydrogen or $C_{1-6}$alkylcarbonyl;

$R^{11}$ is hydrogen; halo or mono-, di- or tri(halo)methyl;

Y is $Y^1$ or $Y^2$, wherein $Y^1$ is a covalent bond; $C_{1-6}$alkanediyl; —$NR^7$— or —$C_{1-6}$alkanediyl-$NR^7$—; or $Y^2$ is —O—, provided that $R^9$ is other than hydroxy or $C_{1-6}$alkyloxy;

$R^4$ and $R^5$ may also be taken together to form a bivalent radical of formula —O—$CH_2$—$CH_2$—O— or —C(=O)—$NR^3$—$CH_2$—$NR^7$—;

$R^6$ is hydroxy; $C_{1-6}$alkyloxy; $C_{1-6}$alkyl or $Ar^3C_{1-6}$alkyl;

$Ar^1$ is phenyl; phenyl substituted with 1, 2 or 3 substituents each independently selected from halo, $C_{1-4}$alkyl, halo$C_{1-4}$alkyl, cyano, aminocarbonyl, $C_{1-4}$alkyloxy or halo$C_{1-4}$alkyloxy;

$Ar^2$ is naphtalenyl; phenyl; phenyl substituted with 1, 2 or 3 substituents each independently selected from hydroxy, halo, cyano, nitro, amino, mono- or di($C_{1-4}$ alkyl)amino, $C_{1-4}$alkyl, halo$C_{1-4}$alkyl, $C_{1-4}$alkyloxy, halo$C_{1-4}$alkyloxy, carboxyl, $C_{1-4}$alkyloxycarbonyl, aminocarbonyl and mono- or di($C_{1-4}$alkyl) aminocarbonyl;

$Ar^3$ is phenyl or phenyl substituted with 1, 2 or 3 substituents selected from halo, hydroxy, amino, nitro, aminocarbonyl, $C_{1-6}$alkyl, halo$C_{1-6}$alkyl or $C_{1-6}$alkyloxy; and Het is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl or mono-, di- or tri(halo)methyl.

The heterocycles in the definition of Het are preferably connected to the rest of the molecule, i.e. X, —C(=Q)— or $C_{1-6}$alkyl, by a carbon atom.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like; $C_{1-6}$alkyl is meant to include $C_{1-4}$alkyl and the higher homologues thereof having 5 to 6 carbon atoms such as, for example, pentyl, 2-methylbutyl, hexyl, 2-methylpentyl and the like; $C_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl, and the like; $C_{1-6}$alkanediyl is meant to include $C_{1-4}$alkanediyl and the higher homologues thereof having from 5 to 6 carbon atoms such as, for example, 1,5-pentanediyl, 1,6-hexanediyl and the like.

As used in the foregoing definitions and hereinafter, halo$C_{1-4}$alkyl is defined as mono- or polyhalosubstituted $C_{1-4}$alkyl, in particular $C_{1-4}$alkyl substituted with 1 to 6 halogen atoms, more in particular difluoro- or trifluoromethyl.

The pharmaceutically acceptable addition salts as mentioned hereinabove are meant to comprise the therapeutically active non-toxic acid addition salt forms which the compounds of formula (I) are able to form. Said salts can conveniently be obtained by treating the base form of the compounds of formula (I) with appropriate acids such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, the metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabanine salts, and salts with amino acids such as, for example, arginine, lysine and the like.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

For isolation and purification purposes, it is also possible to use pharmaceutically unacceptable salts. Only the pharmaceutically acceptable, non-toxic salts are used therapeutically and those salts are therefore preferred.

The term "stereochemically isomeric forms" as used hereinbefore defines all the possible isomeric as well as conformational forms which the compounds of formula (I) may possess. Unless otherwise mentioned or indicated, the chemical designation of compounds denotes the mixture, more in particular the racemic mixture, of all possible stereochemically and conformationally isomeric forms, said mixtures containing all diastereomers, enantiomers and/or conformers of the basic molecular structure. More in particular, stereogenic centers may have the R- or S-configuration; substituents on bivalent cyclic saturated radicals may have either the cis- or trans-configuration; >C=$NR^3$ and $C_{3-6}$alkenyl radicals may have the E- or Z-configuration. For the compounds having two stereogenic centers, the relative stereodescriptors R* and S* are used in accordance with the Chemical Abstracts rules (Chemical Substance Name Selection Manual (CA), 1982 Edition, Vol. III, Chapter 20). All stereochemically isomeric forms of the compounds of formula (I) both in pure form or mixtures thereof are intended to be embraced within the scope of the present invention.

Some of the compounds of formula (I) may also exist in their tautomeric form. Such forms although not explicitly indicated in the above formula are intended to be included within the scope of the present invention. For instance, compounds of formula (I) wherein X is —NH— and =Q is =O or $R^5$ is a radical of formula (a-1) or (a-2), may exist in their corresponding tautomeric form.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-nitrogens are N-oxidized.

Whenever used hereinafter, the term "compounds of formula (I)" is meant to also include their N-oxide forms, their pharmaceutically acceptable addition salts, and their stereochemically isomeric forms.

A special group of compounds are those compounds of formula (I) wherein $R^8$ is hydrogen; $C_{1-6}$alkyl; $Ar^3C_{1-6}$alkyl; di($Ar^3$)$C_{1-6}$alkyl; benzoxazolyl or benzothiazolyl; $R^9$ is hydrogen; hydroxy; $C_{1-6}$alkyl; $C_{1-6}$alkyloxy; $Ar^3$; $Ar^3C_{1-6}$alkyl; di($Ar^3$)$C_{1-6}$alkyl; amino; mono- or di($C_{1-6}$alkyl) amino; pyrrolidinyl; piperidinyl; homopiperidinyl; morpholinyl or thiomorpholinyl; and Het is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl or mono-, di- or tri(halo)methyl.

A first group of interesting compounds consists of those compounds of formula (I) wherein one or more of the following restrictions apply:

a) $R^1$ is $Ar^1C_{1-6}$alkyl; or b) $R^2$ is pyrimidinyl; naphtalenyl; pyrrolyl; furanyl; quinoxalinyl; pyridinyl; indolyl; benzofuranyl; benzothienyl; thiazolyl; thienyl; pyrazinyl; each of said monocyclic and bicyclic heterocycles may optionally be substituted on a carbon atom by 1 or 2 substituents selected from halo, $C_{1-4}$alkyl or mono-, di- or tri(halo) methyl; or $R^2$ is phenyl substituted with 1, 2 or 3 substituents each independently selected from halo, cyano, $C_{1-4}$alkyl, $C_{1-4}$alkyloxy, halo$C_{1-4}$alkyloxy, $C_{1-14}$alkyloxycarbonyl and halo$C_{1-4}$alkyl, in particular, selected from methyl and trifluoromethyl; or phenyl$C_{1-6}$alkyl wherein phenyl in said phenyl$C_{1-6}$alkyl is optionally substituted with 1, 2 or 3 substituents selected from halo and $C_{1-4}$alkyloxy; or c) n is 1; or d) m is 1; or e) =Q is =O; or f) X is a covalent bond or a bivalent radical of formula —S—or —$NR^3$—, in particular a covalent bond.

A second group of interesting compounds consists of those compounds of formula (I) wherein p is 1; $R^4$ is hydrogen; $Ar^3$ or $C_{1-4}$alkyloxy$C_{1-4}$alkyl; $R^5$ is hydroxy; $Ar^3$, di($Ar^3$)$C_{1-6}$alkyloxy; —$NR^7R^8$; $C_{1-6}$alkyl substituted with —$NR^7R^8$; or a radical of formula (a-1) or (a-2); $R^4$ and $R^5$ are taken together to form a bivalent radical of formula —O—$CH_2$—$CH_2$—O— or —C(=O)—$NR^7$—$CH_2$—$NR^7$—; $R^6$ is hydrogen.

Of special interest are those compounds of formula (I) wherein $R^1$ is $Ar^1C_{1-6}$alkyl, $R^2$ is phenyl substituted with 2 substituents selected from methyl or trifluoromethyl, X is a covalent bond and =Q is =O.

Further of special interest are those compounds of formula (I) wherein n and m are 1 and p is 1.

A particular group of compounds consists of those compounds of formula (I) wherein $R^1$ is phenylmethyl; $R^2$ is phenyl substituted with 2 substituents selected from methyl or trifluoromethyl; n and m are 1; X is a covalent bond; and =Q is =O.

Another particular group of compounds consists of those compounds of formula (I) wherein p is 1; $R^4$ is hydrogen; $C_{1-4}$alkyloxy$C_{1-4}$alkyl, phenyl or phenyl substituted with halo; $R^5$ is phenyl; amino substituted with phenyl or substituted imidazolyl; or phenyl substituted with halo; or $R^5$ is a radical of formula (a-1) wherein Y is $Y^1$ or $Y^2$ wherein $Y^1$ is a covalent bond, —$NR^7$— or —$CH_2$—$NR^7$—; wherein $R^7$ is hydrogen or phenyl optionally substituted with halo; $Y^2$ is —O—; $R^9$ is $C_{1-6}$alkyl, $C_{1-6}$alkyloxy, pyrrolidinyl, phenyl$C_{1-6}$alkyl, imidazolyl substituted with phenyl$C_{1-6}$alkyl or $Ar^3$; or $R^5$ is a radical of formula (a-2) wherein $R_{10}$ is hydrogen or $C_{1-6}$alkylcarbonyl; $R^{11}$ is hydrogen; or $R^4$ and $R^5$ are taken together to form a bivalent radical of formula —C(=O)—$NR^3$—$CH_2$—$NR^7$— wherein each $R^7$ independently is selected from hydrogen or phenyl; and $R^6$ is hydrogen.

Preferred compounds are those compounds of formula (I) wherein $R^1$ is phenylmethyl; $R^2$ is phenyl substituted with 2 substituents selected from methyl or trifluoromethyl; n, m and p are 1; X is a covalent bond; =Q is =O; $R^4$ is hydrogen, phenyl or phenyl substituted with halo; $R^5$ is phenyl, phenyl substituted with halo; or $R^5$ is a radical of formula (a-1) wherein Y is $Y^1$ or $Y^2$ wherein $Y^1$ is a covalent bond, —$NR^7$— or —$CH_2$—$NR^7$—; wherein $R^7$ is hydrogen or phenyl optionally substituted with halo; $Y^2$ is —O—; $R^9$ is $C_{1-6}$alkyl, $C_{1-6}$alkyloxy, pyrrolidinyl, phenyl$C_{1-6}$alkyl or $Ar^3$; or $R^5$ is a radical of formula (a-2) wherein $R^{10}$ is hydrogen or $C_{1-6}$alkylcarbonyl; $R^{11}$ is hydrogen; or $R^4$ and $R^5$ are taken together to form a bivalent radical of formula —C(=O)—NH—$CH_2$—$NR^7$— wherein $R^7$ is phenyl; and $R^6$ is hydrogen.

Most preferred are those compounds selected from

1-[3,5-bis(trifluoromethyl)benzoyl]-4-[4-(2,3-dihydro-2-oxo-1H-benzimidazol-1-yl)-1-piperidinyl]-2-(phenylmethyl)piperidine;

1-[3,5-bis(trifluoromethyl)benzoyl]-2-(phenylmethyl)-4-[4-phenyl-4-(1-pyrrolidinylcarbonyl)-1-piperidinyl]piperidine;

N-[[1-[1-[3,5-bis(trifluoromethyl)benzoyl]-2-(phenylmethyl)-4-piperidinyl]-4-phenyl-4-piperidinyl]methyl]acetamide;

1-[3,5-bis(trifluoromethyl)benzoyl]-4-[4-oxo-1-phenyl-1,3,8-triazaspiro[4.5]dec-8-yl]-2-(phenylmethyl)piperidine;

1-[3,5-bis(trifluoromethyl)benzoyl]-4-[4-phenyl-4-(1-pyrrolidinylcarbonyl)-1-piperidinyl]-2-[[4-(trifluoromethyl)phenyl]methyl]piperidine; and 1-[3,5-bis(trifluoromethyl)benzoyl]-2-[(3,4-difluorophenyl)methyl]-4-[4-phenyl-4-(1-pyrrolidinylcarbonyl)-1-piperidinyl]piperidine; and the pharmaceutically acceptable acid addition salts and the stereo isomeric forms thereof.

The compounds of formula (I) can be prepared by reductively N-alkylating an intermediate of formula (III) with an intermediate of formula (II). Said reductive N-alkylation may be performed in a reaction-inert solvent such as, for example, dichloromethane, ethanol, toluene or a mixture thereof, and in the presence of a reducing agent such as, for example, a borohydride, e.g. sodium borohydride, sodium cyano-borohydride or triacetoxy borohydride. In case a borohydride is used as a reducing agent, it may be convenient to use a catalyst such as, for example, titanium(IV) isopropylate as described in J. Org. Chem, 1990, 55, 2552–2554. Using said catalyst may also result in an improved cis/trans ratio in favour of the trans isomer. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

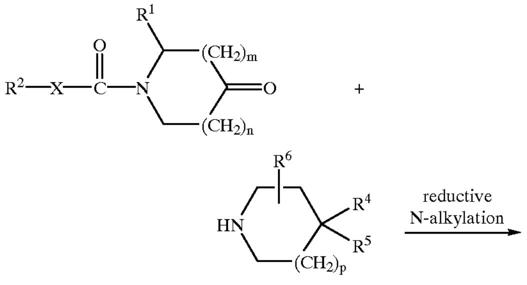

(I)

In this and the following preparations, the reaction products may be isolated from the reaction medium and, if necessary, further purified according to methodologies generally known in the art such as, for example, extraction, crystallization, trituration and chromatography.

The compounds of formula (I) can also be prepared by reacting an intermediate of formula (IV) wherein $W^1$ is an appropriate leaving group such as, for example, a halogen, e.g. chloro or bromo, or a sulfonyloxy leaving group, e.g. methanesulfonyloxy or benzenesulfonyloxy, with an intermediate of formula (V). The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between RT and reflux temperature.

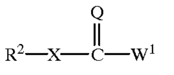

+

(IV)

-continued

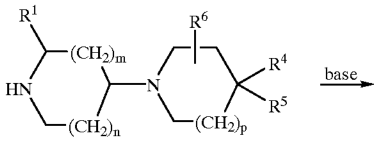

(I)

(V)

The compounds of formula (I) may also be prepared by reacting a piperidinone derivative of formula (VI) with an appropriate organometallic reagent of formula (VII) wherein $R^{4'}$ is the same as $R^4$ but other than hydrogen and M is an organometallic part such as, e.g. —MgBr, yielding compounds of formula (I) wherein $R^5$ is —OH, said compounds being represented by formula (I-a).

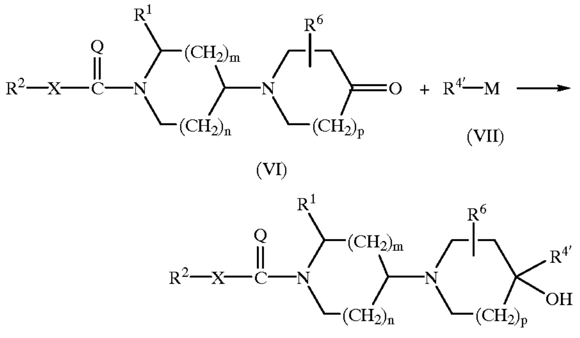

(VI) (VII)

(I-a)

As outlined below, compounds of formula (I) may be converted into each other using art-known transformations.

For instance, compounds of formula (I) wherein $R^5$ is —OH may be converted into compounds of formula (I) wherein $R^5$ is $Ar^3C_{1-6}$alkyloxy, $di(Ar^3)C_{1-6}$alkyloxy or a radical of formula (a-1) wherein Y is O.

Also, compounds of formula (I) wherein $R^5$ is —$NR^7H$ may be converted into compounds of formula (I) wherein $R^5$ is —$NR^7R^8$,$R^8$ being other than hydrogen; or wherein $R^5$ is a radical of formula (a-1) wherein Y is —$NR^7$—.

Further, compounds of formula (I) wherein $R^5$ is a radical of formula (a-2) wherein $R^{10}$ is hydrogen may be converted into compounds of formula (I) wherein $R^5$ is a radical of formula (a-2) wherein $R^{10}$ is a $C_{1-6}$alkylcarbonyl.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For example, intermediates of formula (III), (IV), (VII) and (XI) may be prepared according to art-known procedures.

Intermediates of formula (II) may be prepared by condensing an intermediate of formula (IV) with an intermediate of formula (VIII) analogous to the procedure described in EP-0,532,456-A.

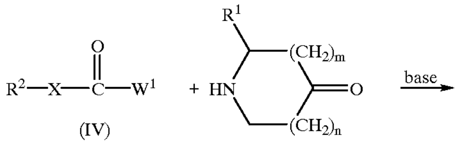

(IV) (VIII) (II)

The preparation of intermediates of formula (VIII) is also described in EP-0,532,456-A. However, intermediates of formula (VIII) wherein $R^1$ is optionally substituted $Ar^1C_{1-6}$alkyl or $di(Ar^1)C_{1-6}$alkyl, said $R^1$ being represented by —$CH(R^{1a})_2$ and said intermediates being represented by formula (VIII-a), may also be prepared as depicted in scheme 1.

Scheme 1

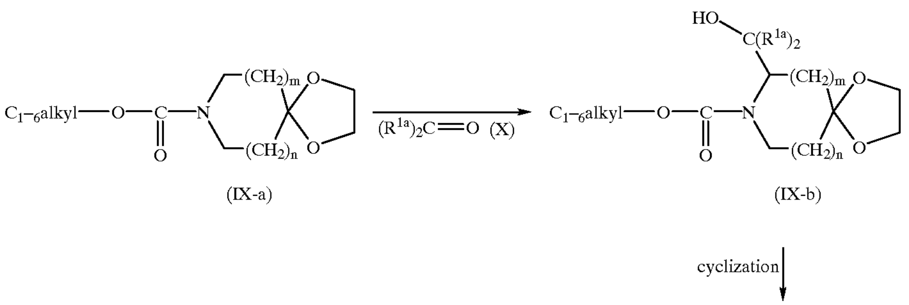

(IX-a) (IX-b)

-continued

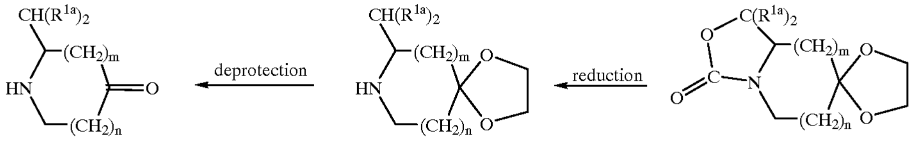

(VIII-a) (IX-d) (IX-c)

In scheme 1, the intermediates of formula (IX-b) may be prepared by reacting an intermediate of formula (IX-a) with an aldehyde or a ketone of formula (X). The $C_{1-6}$alkylcarbamate moiety in the intermediates of formula (IX-b) may be converted into a fused oxazolone which in turn may be reduced to an intermediate of formula (IX-d). Said intermediate (IX-d) may in turn be deprotected, thus forming an intermediate of formula (VIII-a). Subsequently, intermediates of formula (VIII-a) may be reacted with an intermediate of formula (IV) to prepare intermediates of formula (II) wherein $R^1$ is defined as —$CH(R_{1a})_2$, said intermediates being represented by formula (II-a). The reactions performed in scheme 1 may all be conducted following conventional methods that are generally known in the art.

Intermediates of formula (V) may suitably be prepared by reacting an intermediate of formula (VIII-1), being a protected intermediate of formula (VII) with a protecting group $P^1$ such as, for example, a $C_{1-6}$alkyloxycarbonyl group, with an intermediate of formula (III) according to the previously described reductive N-alkylation procedure, and subsequently deprotecting the thus formed intermediate.

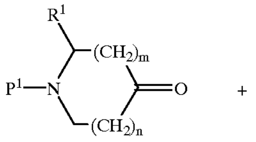

(VIII-1)

-continued

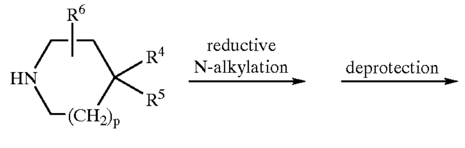

(III)

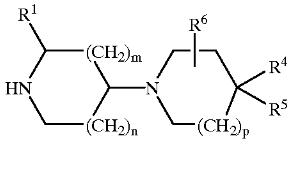

(V)

In particular, intermediates of formula (V) wherein $R^1$ is —$CH(R^{1a})_2$, said intermediates being represented by formula (V-a), may be prepared as is depicted in scheme 2.

Scheme 2

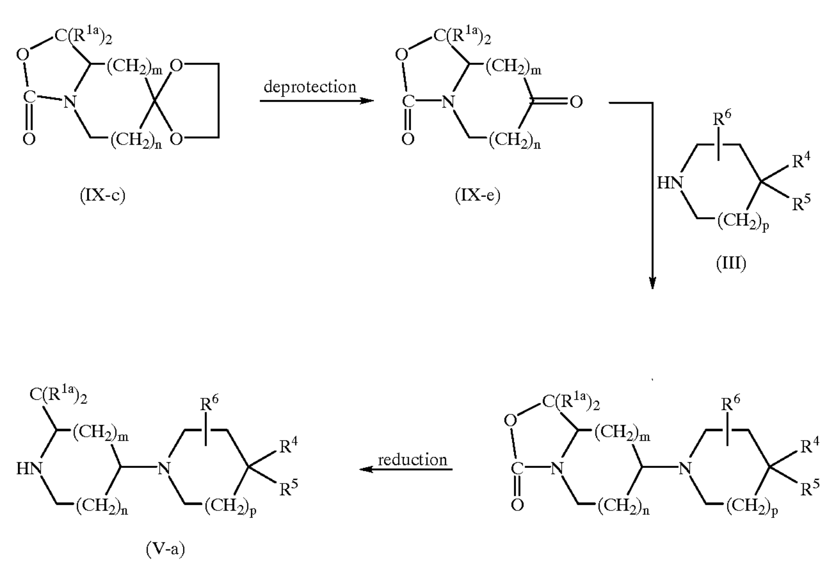

(IX-c) (IX-e) (III) (V-a)

The ketalized intermediate of formula (IX-c) may be transformed to the corresponding ketone of formula (IX-e) which subsequently may be reductively aminated with a pyrrolidine, piperidine- or homopiperidine derivative of formula (III). The thus obtained intermediate may then be reduced with a suitable reducing agent to an intermediate of formula (V-a).

Piperidinone derivatives of formula (VI) may be prepared by reacting an intermediate of formula (II) with an intermediate of formula (XI), according to the previously described N-alkylation procedure, followed by deprotection.

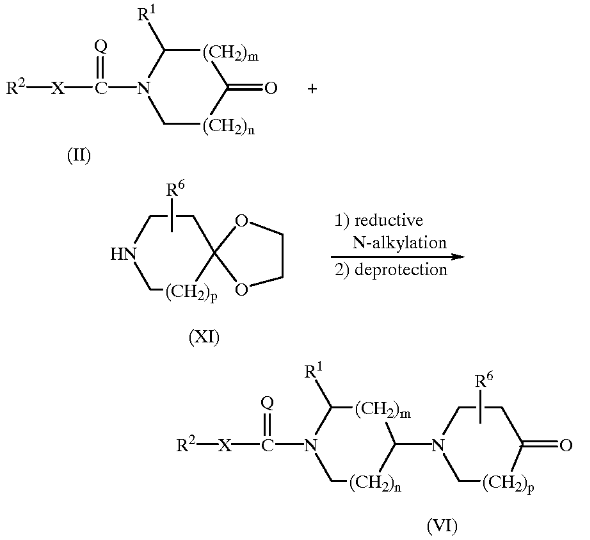

(II) + (XI) → (VI)

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereo-specifically. Preferably if a specific stereoisomer is desired, said compound will be synthesized by stereospecific methods of preparation. These methods will advantageously employ enantiomerically pure starting materials.

The compounds of formula (I) have valuable pharmacological properties in that they interact with tachykinin receptors and they antagonize tachykinin-induced effects, especially substance P-induced effects, both in vivo and in vitro and are thus of use in the treatment of tachykinin-mediated diseases, and in particular in substance P-mediated diseases.

Tachykinins, also referred to as neurokinins, are a family of peptides among which substance P (SP), neurokinin A (NKA), neurokinin B (NKB) and neuropeptide K (NPK) may be identified. They are naturally occurring in mammals, including human beings, and are distributed throughout the central and peripheral nervous system, where they act as neurotransmitters or neuromodulators. Their actions are mediated through several subtypes of receptors, such as, for example, $NK_1$, $NK_2$ and $NK_3$ receptors. Substance P displays highest affinity for $NK_1$ receptors, whereas NKA preferentially binds to $NK_2$ receptors and NKB preferentially binds to $NK_3$ receptors. However, the selectivity of these tachykinins is relatively poor and under physiological conditions the action of any of these tachykinins might be mediated by activation of more than one receptor type.

Substance P and other neurokinins are involved in a variety of biological actions such as pain transmission (nociception), neurogenic inflammation, smooth muscle contraction, plasma protein extravasation, vasodilation, secretion, mast cell degranulation, and also in activation of the immune system. A number of diseases are deemed to be engendered by activation of neurokinin receptors, in particular the $NK_1$ receptor, by excessive release of substance P and other neurokinins in particular cells such as cells in the neuronal plexi of the gastrointestinal tract, unmyelinated primary sensory afferent neurons, sympathetic and parasympathetic neurons and nonneuronal cell types (DN&P 8(1), February 1995, p. 5–23, "Neurokinin Receptors" by Longmore J. et al.; Pharmacological Reviews 46(4), 1994, p. 551–599, "Receptors and Antagonists for Substance P and Related Peptides" by Regoli et al.).

The compounds of the present invention are potent inhibitors of neurokinin-mediated effects, in particular those mediated via the $NK_1$ receptor, and may therefore be described as tachykinin antagonists, especially as substance P antagonists, as indicated in vitro by the antagonism of substance P-induced relaxation of pig coronary arteries which is described hereinafter. The binding affinity of the present compounds for the human, guinea-pig and gerbil neurokinin receptors may be determined in vitro in a receptor binding test using $^3H$-substance P as radioligand. The subject compounds also show substance-P antagonistic activity in vivo as may be evidenced by, for instance, the antagonism of substance P-induced plasma extravasation in guinea-pigs, or the antagonism of drug-induced emesis in ferrets (Watson et al., Br. J. Pharmacol. 115, 84–94, 1995).

In view of their capability to antagonize the actions of tachykinins by blocking the tachykinin receptors, and in particular antagonizing the actions of substance P by blocking the $NK_1$ receptor, the subject compounds are useful in the prophylactic and therapeutic treatment of tachykinin-mediated diseases such as, for example, pain, in particular traumatic pain such as postoperative pain; traumatic avulsion pain such as brachial plexus; chronic pain such as arthritic pain such as occurring in osteo, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS-related neuropathy, occipital neuralgia, geniculate neuralgia, glossopharyngeal neuralgia, reflex sympathetic dystrophy, phantom limb pain; various forms of headache such as migraine, acute or chronic tension headache, temperomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns;

scar pain; itch; and thalamic pain such as post stroke thalamic pain;

respiratory and inflammatory diseases, in particular inflammation in asthma, influenza, chronic bronchitis and rheumatoid arthritis; inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation;

emesis, i.e. nausea, retching and vomiting, including acute emesis, delayed emesis and anticipatory emesis, no matter how emesis is induced, for example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; antimetabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia;

central nervous system disorders, in particular psychoses such as schizophrenia, mania, dementia or other cognitive disorders e.g. Alzheimer's disease; anxiety; AIDS-related dementia; diabetic neuropathy; multiple sclerosis; depression; Parkinson's disease; and dependence on drugs or substances of abuse;

allergic disorders, in particular allergic disorders of the skin such as urticaria, and allergic disorders of the airways such as rhinitis;

gastrointestinal disorders, such as irritable bowel syndrome;

skin disorders, such as psoriasis, pruritis and sunburn;

vasospastic diseases, such as angina, vascular headache and Reynaud's disease;

cerebral ischaemia, such as cerebral vasospasm following subarachnoid haemorrhage stroke, epilepsie, head trauma, spinal cord trauma and ischemic neuronal damage;

fibrosing and collagen diseases, such as scleroderma and eosinophilic fascioliasis;

disorders related to immune enhancement or suppression, such as systemic lupus erythematosus;

rheumatic diseases, such as fibrositis;

neoplastic disorders;

cell proliferation; and cough.

The compounds of the present invention have a favourable metabolic stability and exhibit good oral availability. They also have an advantageous onset and duration of action. The compounds of formula (I) also have the ability to penetrate the central nervous system as may be demonstrated in vivo by their inhibitory effect on the change in behaviour induced by intracerebroventricular-applied substance P in the gerbil.

In view of the utility of the compounds of formula (I), there is provided a method of treating warm-blooded animals, including humans, suffering from tachykinin-mediated diseases as mentioned hereinabove, in particular, pain, emesis or asthma. Said method comprises the systemic administration of an effective tachykinin antagonizing amount of a compound of formula (I), a N-oxide form, a pharmaceutically acceptable addition salt or a possible stereoisomeric form thereof, to warm-blooded animals, including humans. Hence, the use of a compound of formula (I) as a medicine is provided, and in particular a medicine to treat pain, emesis or asthma.

For ease of administration, the subject compounds may be formulated into various pharmaceutical forms for administration purposes. To prepare the pharmaceutical compositions of this invention, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid or base addition salts of compounds of formula (I) due to their increased water solubility over the corresponding base or acid form, are obviously more suitable in the preparation of aqueous compositions.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in the treatment of tachykinin mediated diseases could determine the effective therapeutic daily amount from the test results presented hereinafter. An effective therapeutic daily amount would be from about 0.001 mg/kg to about 40 mg/kg body weight, more preferably from about 0.01 mg/kg to about 5 mg/kg body weight. It may be appropriate to administer the therapeutically effective dose once daily or as two, three, four or more sub-doses at appropriate intervals throughout the day. Said sub-doses may be formulated as unit dosage forms, for example, containing 0.05 mg to 500 mg, and in particular, 0.5 mg to 50 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.

The following examples are intended to illustrate and not to limit the scope of the present invention.

EXPERIMENTAL PART

Hereinafter "THF" means tetrahydrofuran, "DIPE" means diisopropylether, "RT" means room temperature and "DMF" means N,N-dimethylformamide. Of some compounds of formula (I) the absolute stereochemical configuration was not experimentally determined. In those cases the stereochemically isomeric form which was first isolated is designated as "A" and the second as "B", without further reference to the actual stereochemical configuration.

Preparation of the Intermediate Compounds

Example A1 a) A mixture of 1,1-dimethylethyl 1,4-dioxo-8-azaspiro [4.5]-8-carboxylate (0.1 mol) in diethylether (150 ml) and N,N,N'N'-tetramethyl-ethylenediamine (33.2 ml) was cooled on a 2-propanol/$CO_2$ bath under a $N_2$ flow. Sec. buthyllithium (1.3 M; 0.11 mol) was added dropwise at a temperature below −60° C. and the mixture was stirred for 3 hours. A mixture of 3,5-(difluoro)benzaldehyde (0.12 mol) in diethylether (75 ml) was added dropwise. The mixture was stirred slowly overnight and allowed to warm to RT. The mixture was decomposed with water and separated into its layers. The aqueous layer was extracted with $CH_2Cl_2$. The combined organic layer was dried, filtered and the solvent was evaporated, yielding 38.5 g of 1,1-dimethylethyl 7-[(3,4-difluorophenyl)hydroxymethyl]-1,4-dioxo-8-azaspiro [4.5]-8-carboxylate (intermediate 10).

b) A mixture of intermediate 10 (0.1 mol) and 2-methyl-2-propanol, potassium salt (1 g) in toluene (200 ml) was stirred and refluxed for 2 hours. The solvent was evaporated and the residue was taken up in $CH_2Cl_2$/water. The organic layer was separated, dried, filtered and the solvent was evaporated. The residue was purified by column chromatography over silica gel (eluent: $CH_2Cl_2/CH_3OH$ 98/2). The pure fractions were collected and the solvent was evaporated. The residue was suspended in petroleum ether and the precipitate was filtered off and dried, yielding 10 g (32%) of (±)-1'-(3,4-difluorophenyl)tetrahydrospiro[1,3-dioxolan-2,7'(1'H)-[3H]-oxazolo[3,4-a]pyridin]-3-one (intermediate 11).

c) A mixture of intermediate 11 (0.032 mol) in $CH_3OH$ (250 ml) was hydrogenated at 50° C. with palladium on activated carbon (10%; 2 g). After uptake of hydrogen, the catalyst was filtered off and the filtrate was evaporated, yielding 9 g (100%) of 7-[(3,4-difluorophenyl)methyl]-1,4-dioxo-8-azaspiro[4.5]decane (intermediate 12).

d) A mixture of intermediate 12 (0.032 mol) in HCl, (6N; 90 ml) was stirred at 75° C., then cooled. $CH_2Cl_2$ was added and the mixture was alkalized with NaOH at a temperature below 20° C. The organic layer was separated, dried, filtered and the solvent was evaporated. The residue was dried, yielding 7.2 g of 2-[(3,4-difluorophenyl)methyl]-4-piperidinone (intermediate 13). In a similar way as described in procedure d) were prepared:

(±)-2-(phenylmethyl)-4-piperidinone (intermediate 1);

(±)-trans-1-(3,5-dimethylbenzoyl)-4-(4-oxo-1-piperidinyl)-2-(phenylmethyl)piperidine (intermediate 2, mp. 108.4° C.);

(±)-cis-1-(3,5-dimethylbenzoyl)-4-(4-oxo-1-piperidinyl)-2-(phenylmethyl)piperidine (intermediate 3); and 2-[[3-fluoro-5-(trifluoromethyl)phenyl]methyl]-4-piperidinone (intermediate 14).

e) A mixture of intermediate 1 in $CH_2Cl_2$, 3,5-dimethylbenzoyl chloride (7.4 g) and triethylamine (11 ml) was stirred overnight at RT. Dilute NaOH was added. The organic layer was separated, dried, filtered and the solvent evaporated. The residue was crystallized from DIPE yielding 7.44 g (58%) of (±)-1-(3,5)-dimethylbenzoyl)-2-(phenylmethyl)-4-piperidinone (intermediate 4). In a similar way as described in procedure e) were prepared:

(±)-1-[3,5-bis(trifluoromethyl)benzoyl]-2-[[4-(trifluoromethyl)phenyl]methyl]-4-piperidinone (intermediate 15);

(±)-1-[3,5-bis(trifluoromethyl)benzoyl]-2-[(3,4-difluorophenyl)methyl]-4-piperidinone (intermediate 16); and (±)-1-[3,5-bis(trifluoromethyl)benzoyl]-2-[[3-fluoro-5-(trifluoromethyl)phenyl]methyl]-4-piperidinone (intermediate 17).

Example A2

Alternative to the procedure sequence as described in example A1.a) through A1.c), the following procedure may be used. Sec-butyllithium (0.63 mol) was added at −78° C. under $N_2$ flow to a solution of 1,1-dimethylethyl 1,4-dioxo-8-azaspiro[4.5]-8-carboxylate (0.57 mol) and N,N,N',N'-tetramethylethylenediamine (1.14 mol) in $(C_2H_5)_2O$ (1000 ml). One hour after complete addition, a mixture of 3-(trifluoromethyl)benzaldehyde (0.57 mol) in $(C_2H_5)_2O$ (200 ml) was added. The mixture was allowed to warm to RT and then stirred at RT for 16 hours. The solvent was evaporated. A mixture of 2-methyl-2-propanol, potassium salt (0.2 mol) in toluene (500 ml) was added. The mixture was stirred at 80° C. for 5 hours. The solvent was evaporated. The residue was heated with a saturated $NH_4Cl$ solution and extracted with $CH_2Cl_2$. The organic layer was separated, dried, filtered and the solvent was evaporated. The residue was suspended in DIPE, filtered off and dried. This fraction was dissolved in $CH_3OH$ (250 ml) and the mixture was hydrogenated with palladium on activated carbon (10%, 3 g) as a catalyst. After uptake of hydrogen, the catalyst was filtered off and the filtrate was evaporated. The residue was purified over silica gel on a glass filter (eluent: $CH_2Cl_2/CH_3OH$ 95/5). The pure fractions were collected and the solvent was evaporated. This fraction was dissolved in HCl (6N, 100 ml) and $CH_3OH$ (100 ml) and the mixture was stirred at 50° C. for 8 hours. The organic solvent was evaporated. The concentrate was washed with a saturated $K_2CO_3$ solution and extracted with $CH_2Cl_2$. The organic layer was separated, dried, filtered and the solvent was evaporated. The residue was purified over silica gel on a glass filter (eluent: $CH_2Cl_2/CH_3OH$ 95/5). The pure fractions were collected and the solvent was evaporated, yielding 48.5 g (70%) of (±)-2-[[4-(trifluoromethyl)phenyl] methyl]-4-piperidinone (intermediate 18).

Example A3

A mixture of (±)-8-tert-butoxycarbonyl-7-(phenylmethyl)-1,4-dioxa-8-azaspiro[4.5]decane (33.34 g) in HCl, (6 N; 250 ml) was stirred at 70° C. for 1 hour 30 minutes. The mixture was cooled, $CH_2Cl_2$ (100 ml) was added and the mixture was alkalized with NaOH while cooling to RT. The organic layer was separated and the aqueous layer was extracted with $CH_2Cl_2$. Triethylamine (20.2 g), followed by 3,5-bis(trifluoromethyl)benzoyl chloride (27.7 g) dissolved in $CH_2Cl_2$ were added and the mixture was stirred for 2 hours. Water was added and the layers were separated. The organic layer was dried, filtered and evaporated. The residue was crystallized from DIPE, the precipitate was filtered off and dried. The mother layer was evaporated and the residue was crystallized from DIPE. The precipitate was filtered off and dried. The two solid fractions were taken up in water and $CH_2Cl_2$. NaOH was added and the mixture was extracted. The organic layer was dried, filtered off and evaporated, yielding 16.14 g (38%) of (±)-1-[3,5-bis-(trifluoromethyl)benzoyl]-2-(phenylmethyl)-4-piperidinone (intermediate 5, mp. 102.5° C.).

Example A4

Di-tert-butyl dicarbonate (21.8 g) was added to a mixture of intermediate 1 (17 g) in $CH_2Cl_2$ (500 ml) and the mixture was stirred at RT for 48 hours. The mixture was evaporated, the residue was taken up in water and toluene and the organic layer was separated. The aqueous layer was extracted again with toluene. The combined organic layers were dried, filtered and evaporated, yielding 38 g (100%) of (±)-1,1-dimethylethyl 4-oxo-2-(phenylmethyl)-1-piperidinecarboxylate (intermediate 6).

Example A5

Hydrochloric acid in 2-propanol (10 ml) was added to a mixture of (±)-1,-dimethyl ethyl (cis+trans)-4-[4-(2,3-dihydro-2-oxo-1H-benzimidazol-1-yl)-1-piperidinyl]-2-(phenylmethyl)-1-piperidinecarboxylate (12 g) in $CH_3OH$ (100 ml) and the mixture was stirred and refluxed for 2 hours 30 minutes. The solvent was evaporated and the residue was taken up in $CH_2Cl_2$ and water with diluted NaOH. The organic layer was separated, washed with water, dried, filtered and evaporated. The residue was purified by column chromatography over silica gel (eluent : $CH_2Cl_2/(CH_3OH/NH_3)$ 93/7). A first fraction was collected and evaporated, yielding 2.1 g (±)-cis-1,3-dihydro-1-[1-[2-(phenylmethyl)-4-piperidinyl]-4-piperidinyl]-2H-benzimidazol-2-one (intermediate 7). A second fraction was collected and evaporated, yielding 0.9 g (±)-trans-1,3-dihydro-1-[1-[2-(phenylmethyl)-4-piperidinyl]-4-piperidinyl]-2H -benzimidazol-2-one (intermediate 8).

Example A6

4-(Methoxymethyl)-N-phenyl-1-(phenylmethyl)-4-piperidinamine (15 g) was hydrogenated in $CH_3OH$ (250 ml) with palladium on activated carbon (10%; 3 g) as a catalyst. After uptake of $H_2$, the catalyst was filtered off. The filtrate was evaporated and the residue was dissolved in 2-propanol (300 ml) and converted into the hydrobromic acid salt (1:2) with hydrobromic acid in acetic acid. This mixture was stirred for 1 hour. DIPE (200 ml) was added and the resulting mixture was stirred for 1 hour. The precipitate was filtered off, washed with DIPE and recrystallized from ethanol/DIPE 3/1. The crystals were filtered off and dried, yielding 12.9 g (70%) of 4-(methoxymethyl)-N-phenyl-4-piperidinamine dihydrobromide (intermediate 9, mp. 220.0° C.).

Example A7 a) A mixture of (±)-1,1-dimethylethyl 4-oxo-2-(phenylmethyl)-1-piperidine carboxylate (0.1 mol) and N-(4-phenyl-4-piperidinyl)acetamide (0.1 mol) in 2-propanol (500 ml) was hydrogenated at 50° C. with platinum (4 g) as a catalyst in the presence of titanium(IV) isopropoxide (28.5 g) and thiophene (4%; 1 ml). After uptake of hydrogen, the catalyst was filtered off and the filtrate was evaporated. The residue was purified by column chromatography over silica gel (eluent: $CH_2Cl_2/CH_3OH$ 97/3). The pure fractions were collected and the solvent was evaporated, yielding 40 g (74.1%) of (±)-1,1-dimethylethyl 4-[4-(acetylamino)-4-phenyl-1-piperidinyl]-2-(phenylmethyl)-1-piperidinecarboxylate (intermediate 19).

b) A mixture of intermediate 19 (0.081 mol) in $CH_3OH$ (300 ml) and 2-propanol in HCl (30 ml) was stirred and refluxed for 2 hours. The solvent was evaporated The residue was taken up in water/DIPE and the mixture was separated into its layers. The aqueous layer was alkalized with NaOH and $CH_2Cl_2$ was added. The combined organic layer was washed with water, dried, filtered and the solvent was evaporated. The residue was purified by column chromatography over silica gel (eluent: $CH_2Cl_2/(CH_3OH/NH_3)$ 95/5). Two pure fractions were collected and their solvents were evaporated, yielding 3 g of fraction 1, 2 g fraction 2 and 2.5 g of (±)-N-[1-[2-(phenylmethyl)-4-piperidinyl]-4-phenyl-4-piperidinyl]acetamide (intermediate 20). Fraction 1 was dissolved in 2-propanol and converted into the hydrochloric acid salt (1:2) with HCl/2-propanol. The precipitate was filtered off and dried, yielding 0.24 g (±)-cis-N-[1-[2-(phenylmethyl)-4-piperidinyl]-4-phenyl-4-piperidinyl] acetamide dihydrochloride. dihydrate (intermediate 21). Intermediate 20 was repurified by column chromatography oversilica gel (eluent: $CH_2Cl_2/(CH_3OH/NH_3)$ 95/5). The pure fractions were collected and the solvent was evaporated The residue was dissolved in 2-propanol and converted into the hydrochloric acid salt (1:2) with HCl/2-propanol. The precipitate was filtered off and dried, yielding 0.44 g of (±)-trans-N-[4-phenyl-1-[2-(phenylmethyl)-4-piperidinyl]-4-piperidinyl]acetamide dihydrochloride.dihydrate (intermediate 22). Less pure fractions (20 g) were repurified by HPLC over silica gel (eluent: $CH_2Cl_2/(CH_3OH/NH_3)$ 95/5). Two pure fraction groups were collected and their solvent was evaporated, yielding 6.5 g (±)-cis-N-[4-phenyl-1-[2-(phenylmethyl)-4-piperidinyl]-4-piperidinyl]acetamide (intermediate 23) and 7.2 g (±)-trans-N-[1-[2-(phenylmethyl)-4-piperidinyl]-4-phenyl-4-piperidinyl] acetamide (intermediate 24).

In a similar way were prepared:

(±)-trans-1-[[1-[4-phenyl-2-(phenylmethyl)-4-piperidinyl]-4-piperidinyl]carbonyl]pyrrolidine (E)-2-butenedioate (1:2) (intermediate 25);

(±)-cis-1-[[1-[4-phenyl-2-(phenylmethyl)-4-piperidinyl]-4-piperidinyl]carbonyl]pyrrolidine (E)-2-butenedioate(1:2) (intermediate 26);

(±)-cis-1-[[1-[4-phenyl-2-(phenylmethyl)-4-piperidinyl]-4-piperidinyl]carbonyl]pyrrolidine (intermediate 27); and (±)-trans-1-[[1-[4-phenyl-2-(phenylmethyl)-4-piperidinyl]-4-piperidinyl]carbonyl]pyrrolidine (intermediate 28).

Example A8 a) 4-Oxo-1-piperidinecarboxylic acid 1,1-dimethylethyl ester (0.053 mol), 1-[(4-fluorophenyl)methyl]-1H-imidazol-2-amine and titanium(IV)isopropoxyde (0.055 mol) were stirred at 50° C. for 2 hours. Ethanol (350 ml) and sodium borohydride (0.53 mol) were added. The mixture was stirred at RT overnight and water was added. The mixture was filtered over decalite, washed with ethanol/$CH_2Cl_2$ and the solvent was evaporated. The residue was taken up in $CH_2Cl_2$, dried, filtered and the solvent was evaporated. The residue was purified over silica gel on a glass filter (eluent: $CH_2Cl_2/CH_3OH$ 100/0, 99/1, 98/2, 97/3, 96/4 and 94/6). The pure fractions were collected and the solvent was evaporated. The residue was crystallized from DIPE and the precipitate was filtered off and dried, yielding 11.3 g (57%) of 1,1-dimethylethyl 4-[[1-[(4-fluorophenyl)methyl]-1H-imidazol-2-yl]amino]-1-piperidinecarboxylate (intermediate 29).

b) A mixture of intermediate 29 (0.026 mol) in a solution of HCl in 2 propanol (15 ml) and $CH_3OH$ (110 ml) was stirred and refluxed for 1 hour. The solvent was evaporated. The residue was taken up in $H_2O/CH_2Cl_2$. The mixture was alkalized with NaOH. The organic layer was separated, dried, filtered and the solvent was evaporated, yielding 4.95 g (69%) of N-[1-[(4-fluorophenyl)methyl]-1H-imidazol-2-yl]-4-piperidinamine (intermediate 30).

Preparation of the Compounds of Formula (I)

Example B1 a) Titanium(IV)isopropoxide (18 g) was added to 4-hydroxypiperidine (5 g) and intermediate 4 (16 g) in $CH_2Cl_2$ (25 ml) and the mixture was stirred at RT for 3 hours. Sodium cyanoborohydride (2 g) dissolved in ethanol (50 ml) was added and the mixture was stirred at RT overnight. Water (50 ml) and $CH_2Cl_2$ (1000 ml) were added, the mixture was filtered through celite, washed with $CH_2Cl_2$ and the filtrate was evaporated. The residue was purified by column chromatography over silica gel (eluent: $CH_2Cl_2$/$CH_3OH$ 96/4). The pure fractions were collected and evaporated, yielding 8.3 g (41%) of (±)-cis-1-(3,5-dimethylbenzoyl)-4-(4-hydroxy-1-piperidinyl)-2-(phenylmethyl)piperidine (compound 30) and 4.1 g (20%) of (±)-trans-1-(3,5-dimethylbenzoyl)-4-(4-hydroxy-1-piperidinyl)-2-(phenylmethyl)piperidine (compound 31).

b) A mixture of intermediate 5 (0.01 mol), 4-[[1-[(4-fluorophenyl)methyl]-1H-benzimidazol-2-yl]methyl]-4-piperidinol (0.01 mol) and titanium(IV)isopropoxide (0.011 mol) in 2-propanol (5 ml) was stirred at 40° C. for 2.5 hours and then cooled. Ethanol (100 ml) and sodiumborohydride were added. The mixture was heated to 50° C. and sodiumborohydride (0.05 mol) was added over a 3 hour period. The mixture was stirred at RT overnight. Water (30 ml) was added and the mixture was stirred for 30 seconds and then filtered over decalite. The decalite was washed with $CH_2Cl_2$, dried and filtered, to give mixture 1. The filtrate was evaporated and the residue was taken up in $CH_2Cl_2$, dried and filtered, to give mixture 2. Mixture 1 and 2 were combined and the solvent was evaporated. The residue was purified by column chromatography over RP 18 (eluent: ammoniumacetate (0.5% in $H_2O$)/$CH_3OH/CH_3CN$ 70/15/15 to $CH_3OH/CH_3CN$ 50/50 to $CH_3CN$ 100%). Two pure fractions were collected and their solvents were evaporated, yielding 2.9 g of (±)-cis-1-[3,5-bis(trifluoromethyl) benzoyl]-4-[4-[[1-[(4-fluorophenyl)methyl]-1H-benzimidazol-2-yl]methyl]-4-hydroxy-1-piperidinyl]-2-(phenylmethyl)piperidine (39%) (compound 74) and 3 g(40%) of (±)-trans-1-[3,5-bis(trifluoromethyl)benzoyl]-4-[4-[[1-[(4-fluorophenyl)-methyl]-1H-benzimidazol-2-yl] methyl]-4-hydroxy-1-piperidinyl]-2-(phenylmethyl)-piperidine (compound 75).

c) A solution of intermediate 15 (0.01 mol), 1-(4-phenyl-4-piperidinylcarbonyl)pyrrolidine hydrochloride (0.01 mol) and triethylamine (0.015 mol) in THF (10 ml) and titanium (IV)isopropoxide (3.72 ml) was stirred at RT for 4 hours. Ethanol (10 ml) and sodium cyanoborohydride (0.01 mol) were added. The mixture was stirred for a few hours. Ice and ethanol (10 ml) were added and the mixture was stirred at RT for 30 minutes and then filtered over decalite. The solvent was evaporated and the residue extracted with $CH_2Cl_2$. The organic layer was separated, dried, filtered and the solvent was evaporated. The residue was purified by HPLC over silica gel (eluent: $CH_2Cl_2/CH_3OH$ 95/5). Two pure fractions were collected and their solvents were evaporated. The residue was crystallized from DIPE. The precipitate was filtered off and dried, yielding 4.07 g of (±)-cis-1-[3,5-bis (trifluoromethyl)-benzoyl]-4-[4-phenyl-4-(1-pyrrolidinylcarbonyl)-1-piperidinyl]-2-[[4-(trifluoromethyl)-phenyl]methyl]piperidine (55%) (compound 111) and 1.3 g of (±)-trans-1-[3,5-bis (trifluoromethyl)benzoyl]-4-[4-phenyl-4-(1-pyrrolidinylcarbonyl)-1-piperidinyl]-2-[[4-(trifluoromethyl) phenyl]methyl]-piperidine (18%) (compound 112).

Example B2

A mixture of intermediate 2 (14.6) and benzenemethanamine (3.9 g) in $CH_3OH$ (250 ml) and thiophene (4%; 1 ml) was hydrogenated at 50° C. overnight with palladium on activated carbon (10%; 2 g) as a catalyst. The catalyst was filtered off and the filtrate was evaporated. The residue was taken up in $CH_3OH$ (250 ml) and hydrogenated further at RT overnight with palladium on activated carbon (10%; 2 g) as a catalyst. After uptake of hydrogen, the catalyst was filtered off and the filtrate was evaporated. The residue was purified by column chromatography over silica gel (eluent: $CH_2Cl_2$/ ($CH_3OH/NH_3$) 95/5). The pure fractions were collected and evaporated, yielding 9.1 g (62%) of (±)-trans-4-(4-amino-1-piperidinyl)-1-(3,5-dimethylbenzoyl)-2-(phenylmethyl) piperidine (compound 22).

Example B3

A mixture of intermediate 2 (2 g) and 2-methoxybenzylamine (0.7 g) in $CH_3OH$ (150 ml) was hydrogenated overnight at 50° C. with palladium on activated carbon (10%; 1 g) as a catalyst in the presence of thiophene (4% solution; 1 ml). After uptake of hydrogen, the catalyst was filtered off and the filtrate was evaporated. The residue was purified by HPLC over silica gel (eluent: from 100% $CH_2Cl_2$ to 100% $CH_2Cl_2/CH_3OH$ (90/10) over 20 minutes at 125 ml/minute). The desired fractions were collected and the solvent was evaporated. The residue was dried, yielding 0.1 g (3.9%) of (±)-trans-1-(3,5-dimethylbenzoyl)-4-[4-[[(2-methoxyphenyl)methyl]-amino]-1-piperidinyl]-2-(phenylmethyl)piperidine (compound 35, mp. 71.2 ° C.).

Example B4

A mixture of compound 3 (2 g), phenylethyl methanesulfonate (1 g) and sodium carbonate (0.75 g) in ethanol (50 ml) was stirred and refluxed overnight. The solvent was evaporated, the residue was taken up in water and extracted with $CH_2Cl_2$. The organic layer was dried, filtered and evaporated. The residue was purified by column chromatography over silica gel (eluent: $CH_2Cl_2/CH_3OH$ 95/5). The pure fractions were collected and the solvent evaporated. The residue was dried, yielding 0.61 g (24%) of (±)-trans-1-(3,5-dimethylbenzoyl)-4-[4-[(2-phenylethyl)amino]-1-piperidinyl]-2-(phenylmethyl)piperidine (compound 27, mp. 67.8° C.).

Example B5

3,5-Dichlorobenzoyl chloride (1 g) was added to a mixture of compound 31 (2 g) and triethylamine (0.5 g) in $CH_2Cl_2$ (25 ml) and the mixture was stirred at RT for 1 hour. The mixture was washed with water. The organic layer was dried, filtered and the solvent was evaporated. The residue was purified by column chromatography over silica gel (eluent: $CH_2Cl_2/CH_3OH$ 97/3). The pure fractions were collected and their solvent evaporated. The residue was dried, yielding 0.34 g (11.7%) of(±)-trans-1-[1-(3,5-dimethylbenzoyl)-2-(phenylmethyl)-4-piperidinyl]-4-piperidinyl 3,5-dichloro-benzoate (compound 33, mp. 83.3° C.).

Example B6

Using the same reaction procedure as described in example B5, 3,5-bis(trifluoromethyl)benzoyl chloride was reacted with intermediate 8 to form (±)-trans-1-[3,5-bis (trifluoromethyl)benzoyl]-4-[4-(2,3-dihydro-2-oxo-1H-benzimidazol-1-yl)-1-piperidinyl]-2-(phenylmethyl) piperidine (compound 43, mp. 156.1° C.).

Example B7

Using the same reaction procedure as described in example B6, 3,5-dimethylbenzoyl chloride was reacted with compound 22 to form (±)-trans-N-[1-[1-(3,5-dimethylbenzoyl)-2-(phenylmethyl)-4-piperidinyl]-4-piperidinyl]-3,5-dimethylbenzamide (compound 21, mp. 120.1° C.).

Example B8

Using the same reaction procedure as described in example B6, propionyl chloride was reacted with (±)-cis-4-[4-(2,3-dihydro-2-oxo-1H-benzimidazol-1-yl)-1-piperidinyl]-1-(3,5-dimethylbenzoyl)-2-(phenylmethyl) piperidine to form (±)-cis-1-[1-[1-(3,5-di-methylbenzoyl)-2-(phenyl-methyl)-4-piperidinyl]-4-piperidinyl]-1,3-dihydro-3-(1-oxopropyl)-2H-benzimidazol-2-one (compound 34).

Example B9

Magnesium turnings (0.25 g) in THF were stirred and refluxed. 2-Bromoanisole (0.9 g) dissolved in THF (15 ml) was added dropwise and the mixture was stirred and refluxed for 3 hours. Intermediate 2 (2.7 g) dissolved in THF (15 ml) was added and the mixture was stirred and refluxed overnight. The mixture was washed with water, the layers were separated and the aqueous layer was extracted with $CH_2Cl_2$. The combined organic layers were dried, filtered and evaporated. The residue was dried and further purified by HPLC (eluent: $CH_2Cl_2/CH_3OH$ 100/0 to 98/2). The pure fractions were collected and evaporated. The residue was suspended in water/$CH_3OH$/$CH_3CN$ 30/40/40, filtered off and dried, yielding 0.2 g (5.8%) of (±)-trans-1-(3,5-dimethylbenzoyl)-4-[4-hydroxy-4-(2-methoxyphenyl)-1-piperidinyl]-2-(phenyl-methyl)piperidine (compound 17, mp. 213.1° C.).

Example B10

A solution of (±)-ethyl cis-1-[1-(3,5-dimethylbenzoyl)-2-(phenylnethyl)-4-piperidinyl]-4-phenyl-4-piperidinecarboxylate (2.96 g) in NaOH (20 ml) and dioxane (50 ml) was stirred and refluxed for 30 hours. The mixture was evaporated and HCl, (1 N; 20 ml) was added. The precipitate was filtered off, water (100 ml) and $CH_2Cl_2$ (10 ml) were added and filtered again. The precipitate was taken up in water, heated, cooled, filtered off and dried. The product was purified by HPLC (eluent: ammoniumacetate and $CH_3CN$). The pure fractions were collected, evaporated and dried, yielding 1.09 g (39%) of (±)-cis-1-[1-(3,5-dimethylbenzoyl)-2-(phenylmethyl)-4-piperidinyl]-4-phenyl-4-piperidinecarboxylic acid (compound 38, mp. 259.1° C.).

Example B11

A mixture of (±)-cis-4-(4-amino-1-piperidinyl)-1-(3,5-dimethylbenzoyl)-2-(phenylmethyl)piperidine (4 g) and 2H,3H-1,3-benzoxazine-2,6-dione (1.6 g) in DMF (100 ml) was stirred and heated at 80° C. for 4 hours. The mixture was evaporated and the residue was purified by column chromatography over silica gel (eluent: $CH_2Cl_2/CH_3OH$ 98/2). The pure fractions were collected and evaporated. The residue was dried, yielding 1.34 g (25.5%) of (±)-cis-2-amino-N-[1-[1-(3,5-dimethylbenzoyl)-2-(phenylmethyl)-4-piperidinyl]-4-piperidinyl]benzamide (compound 24, mp. 121.1 ° C.).

Example B12

2,4-dimethyl-5-thiazoic acid(0.080 g) and 1H-benzotriazol-1-ol (0.060 g) were added to intermediate 22 (0.100 g) in $CH_2Cl_2$ (5 ml). The mixture was stirred and cooled on an ice-bath, under $N_2$ flow. Triethylamine was added dropwise. A solution of $(CH_3)_2$—N—$(CH_2)_3$—N═N—$CH_2$—$CH_3$ (0.080 g) in $CH_2Cl_2$ (5 ml) was added dropwise and the reaction mixture was allowed to warm to RT, under $N_2$. The reaction mixture was stirred overnight. Then, the compound was isolated and purified by column chromatography (eluent: (0.5% ammoniumacetate in $H_2O$)/$CH_3OH$/$CH_3CN$ 70/15/15 upgrading to 0/0/100). The desired fractions were collected and the solvent was evaporated, yielding 0.070 g of (±)-trans-N-[1-[1-[(2,4-dimethyl-5-thiazolyl)carbonyl]-2-(phenylmethyl)-4-piperidinyl]-4-phenyl-4-piperidinyl]acetamide (compound 121).

Example B13

A mixture of (±)-1-[3,5-bis(trifluoromethyl)benzoyl]-2-(phenylmethyl)-4-piperidinone (0.018 mol), intermediate 30 (0.018 mol) and titanium(IV)isopropoxide (0.018 mol) in 2-propanol (150 ml) was hydrogenated at 50° C. with platinum on activated carbon 5% (2 g) as a catalyst in the presence of a thiophene solution (1 ml). After uptake of hydrogen, the catalyst was filtered off and the filtrate was evaporated. The residue was taken up in $H_2O$ and $CH_2Cl_2$, filtered over decalite and washed several times with $H_2O$. The organic layer was separated, dried, filtered and the solvent was evaporated. The residue was purified by HPLC over silica gel (eluent: $CH_2Cl_2/CH_3OH/(CH_3OH/NH_3)$ 95/4.5/0.5). Two pure fractions were collected and their solvents were evaporated. The residue was dried, yielding 1.02 g of (±)-cis-1-[3,5-bis(trifluoromethyl)benzoyl]-4-[4-[[1-[(4-fluorophenyl)methyl]-1H-imidazol-2-yl]amino]-1-piperidinyl]-2-(phenylmethyl)-piperidine (compound 72) and 0.77 g (6%) of (±)-trans-1-[3,5-bis(trifluoromethyl)-benzoyl]-4-[4-[[1-[(4-fluorophenyl)methyl]-1H-imidazol-2-yl]amino]-1-piperidinyl]-2-(phenylmethyl)piperidine (compound 73).

Example B14

A mixture of intermediate 23 (0.0025 mol) and 3,5-di(trifluoromethyl)-1-isocyanatobenzene (0.0025 mol) in $CH_2Cl_2$ (25 ml) was stirred at RT overnight. The solvent was evaporated and the residue was crystallized from $CH_3CN$. The precipitate was filtered off and dried, yielding: 0.88 g (54%) of (±)-cis-4-[4-(acetylamino)-4-phenyl-1-piperidinyl]-N-[3,5-bis(trifluoromethyl)phenyl]-2-(phenylmethyl)-1-piperidinecarboxamide (compound 127).

The following tables list compounds of formula (I) as prepared according to one of the above examples (Ex.).

TABLE 1

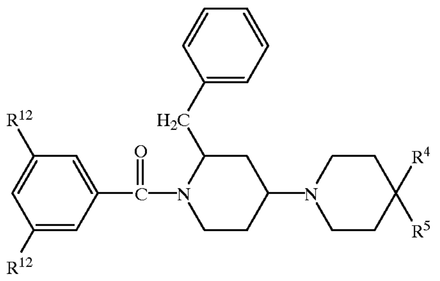

| Co. No. | Ex. No. | $R^{12}$ | $R^4$ | $R^5$ | Physical data |
|---|---|---|---|---|---|
| 1 | B2 | $CH_3$ | 4-chlorophenyl | —OH | (±)-cis; mp. 162.1° C. |
| 2 | B1a | $CH_3$ | phenyl | —NH—CO—$CH_3$ | (±)-cis; mp. 131.4° C. |
| 3 | B1a | $CH_3$ | phenyl | —NH—CO—$CH_3$ | (±)-trans; mp. 128.5° C. |
| 4 | B2 | $CH_3$ | H | 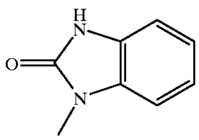 | (±)-cis; mp. 145.5° C. |
| 5 | B2 | $CH_3$ | H | 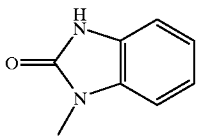 | (±)-trans; mp. 161.9° C. |
| 6 | B2 | $CH_3$ | —$CH_2$—O—$CH_3$ | aminophenyl | (±)-cis; mp. 144.3° C. |
| 6a | B2 | $CH_3$ | —$CH_2$—O—$CH_3$ | aminophenyl | (±)-trans |
| 7 | B1a | $CH_3$ | H | 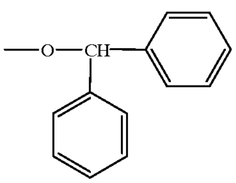 | (±)-cis; mp. 71.3° C. |
| 8 | B1a | $CH_3$ | H | —O—$CH(C_6H_5)_2$ | (±)-trans; mp. 85.8° C. |
| 9 | B1a | $CH_3$ | phenyl | phenyl | (A) |
| 10 | B1a | $CH_3$ | phenyl | phenyl | (B) |
| 11 | B1a | $CH_3$ | 4-chlorophenyl | —C(=O)—$CH_2$—$C_6H_5$ | |
| 12 | B1a | $CH_3$ | H | 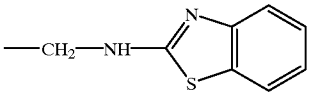 | (A) |

TABLE 1-continued
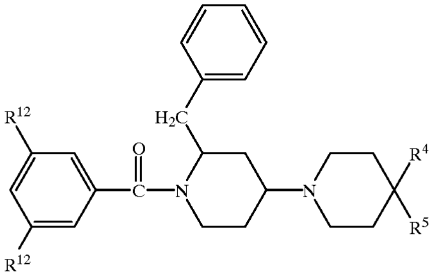
| Co. No. | Ex. No. | $R^{12}$ | $R^4$ | $R^5$ | Physical data |
|---|---|---|---|---|---|
| 13 | B1a | $CH_3$ | H | 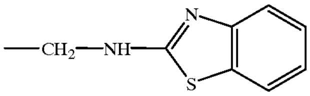 | (B) |
| 14 | B1a | $CH_3$ | phenyl | $—CH_2—NH—CO—CH_3$ | (A) |
| 15 | B1a | $CH_3$ | phenyl | $—CH_2—NH—CO—CH_3$ | (B) |
| 16 | B9 | $CH_3$ | 3-methoxyphenyl | OH | (±)-cis; mp. 102.1° C. |
| 17 | B9 | $CH_3$ | 3-methoxyphenyl | OH | (±)-trans; mp. 213.1° C. |
| 18 | B7 | $CH_3$ | H | 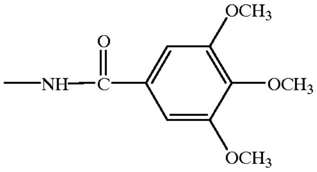 | (±)-cis; mp. 130.1° C. |
| 19 | B7 | $CH_3$ | H | 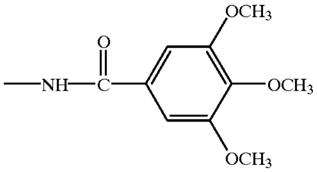 | (±)-trans; mp. 131.5° C. |
| 20 | B7 | $CH_3$ | H | 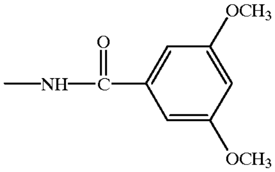 | (±)-cis; mp. 100.2° C. |
| 21 | B7 | $CH_3$ | H | 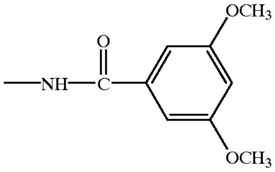 | (±)-trans; mp. 120.1° C. |
| 22 | B2 | $CH_3$ | H | $—NH_2$ | (±)-trans; |
| 23 | B2 | $CH_3$ | H | $—NH_2$ | (±)-cis |
| 24 | B11 | $CH_3$ | H | 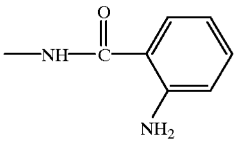 | (±)-cis; mp. 121.1° C. |

TABLE 1-continued
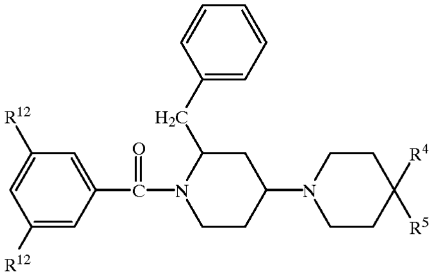
| Co. No. | Ex. No. | $R^{12}$ | $R^4$ | $R^5$ | Physical data |
|---|---|---|---|---|---|
| 25 | B11 | $CH_3$ | H | 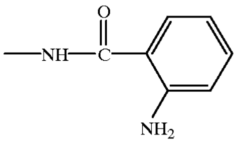 | (±)-trans; mp. 256.6° C. |
| 26 | B4 | $CH_3$ | H | $—NH—(CH_2)_2—C_6H_5$ | (±)-cis; mp. 224.5° C. |
| 27 | B4 | $CH_3$ | H | $—NH—(CH_2)_2—C_6H_5$ | (±)-trans; mp. 67.8° C. |
| 28 | B1a | $CH_3$ | H | 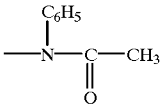 | (±)-cis; mp. 88.3° C. |
| 29 | B1a | $CH_3$ | H | 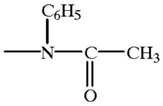 | (±)-trans; mp. 91.6° C. |
| 30 | B1a | $CH_3$ | H | OH | (±)-cis; |
| 31 | B1a | $CH_3$ | H | OH | (±)-trans; |
| 32 | B5 | $CH_3$ | H | 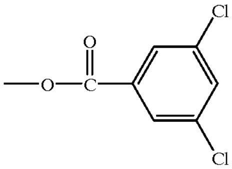 | (±)-cis; mp. 68.2° C. |
| 33 | B5 | $CH_3$ | H | 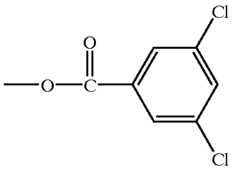 | (±) trans; mp. 83.3° C. |
| 34 | B8 | $CH_3$ | H | 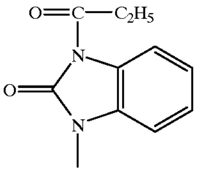 | (±)-cis |
| 35 | B3 | $CH_3$ | H | 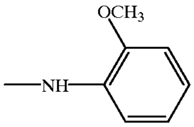 | (±)-trans; mp. 71.2° C. |

TABLE 1-continued

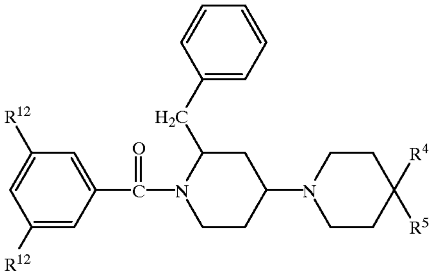

| Co. No. | Ex. No. | $R^{12}$ | $R^4$ | $R^5$ | Physical data |
|---|---|---|---|---|---|
| 36 | B2 | $CH_3$ | phenyl | $—C(=O)—O—C_2H_5$ | (±)-cis; mp. 133.6° C. |
| 37 | B2 | $CH_3$ | phenyl | $—C(=O)—O—C_2H_5$ | (±)-trans; |
| 38 | B10 | $CH_3$ | phenyl | —C(=O)—OH | (±)-cis; mp. 259.1° C. |
| 39 | B1a | $CF_3$ | 4-chlorophenyl | OH | (A) |
| 40 | B1a | $CF_3$ | 4-chlorophenyl | OH | (B) |
| 41 | B1a | $CF_3$ | H | 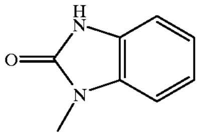 | (±) |
| 42 | B6 | $CF_3$ | H | 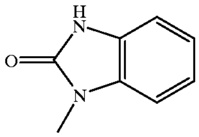 | (±)-cis; mp. 159.2° C. |
| 43 | B6 | $CF_3$ | H | 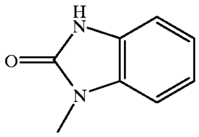 | (±)-trans; mp. 156.1° C. |
| 44 | B1a | $CF_3$ | H | $—O—CH(C_6H_5)_2$ | (A) |
| 45 | B1a | $CF_3$ | H | $—O—CH(C_6H_5)_2$ | (B) |
| 46 | B1a | $CF_3$ | phenyl | 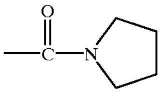 | (±)-(cis + trans) |
| 47 | B1a | $CF_3$ | phenyl | 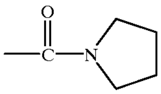 | (±)-cis; mp. 127.0° C. |
| 48 | B1a | $CF_3$ | phenyl | 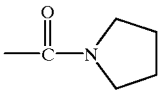 | (±)-trans; mp. 137.8° C. |
| 49 | B1a | $CF_3$ | phenyl | $—CH_2—NH—CO—CH_3$ | (±) |
| 50 | B1a | $CF_3$ | phenyl | phenyl | (A) |
| 51 | B1a | $CF_3$ | phenyl | phenyl | (B) |

TABLE 1-continued
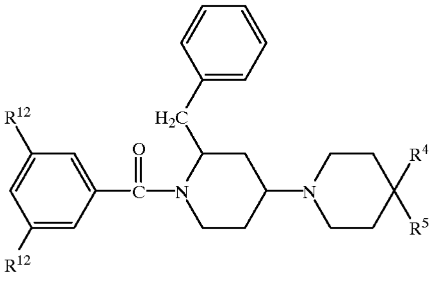
| Co. No. | Ex. No. | $R^{12}$ | $R^4$ | $R^5$ | Physical data |
|---|---|---|---|---|---|
| 52 | B1a | $CF_3$ | H | 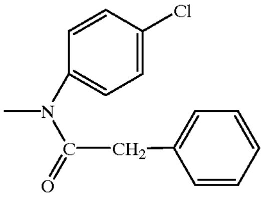 | (A) |
| 53 | B1a | $CF_3$ | H | 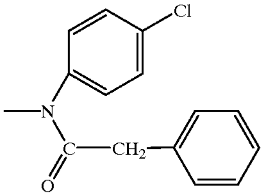 | (B) |
| 54 | B1a | $CF_3$ | H | 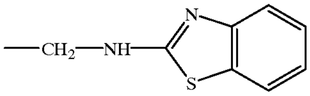 | (A) |
| 55 | B1a | $CF_3$ | H | 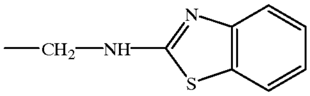 | (B) |
| 60 | B1a | $CF_3$ | H | 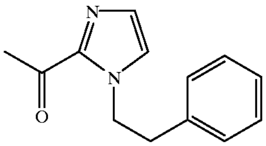 | (±)-cis |
| 61 | B1a | $CF_3$ | H | 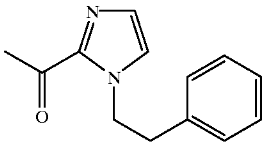 | (±)-trans |
| 62 | B6 | F | phenyl | $—NH—C(=O)—CH_3$ | (±)-cis |
| 63 | B6 | Cl | phenyl | $—NH—C(=O)—CH_3$ | (±)-cis |
| 64 | B6 | Cl | phenyl | $—C(=O)—O—C_2H_5$ | (±)-cis |
| 65 | B6 | H | phenyl | $—NH—C(=O)—CH_3$ | (±)-cis |
| 66 | B6 | Cl | phenyl | $—C(=O)—O—C_2H_5$ | (±)-trans |
| 67 | B6 | H | phenyl | $—C(=O)—O—C_2H_5$ | (±)-trans |
| 68 | B6 | F | phenyl | $—C(=O)—O—C_2H_5$ | (±)-trans |

TABLE 1-continued
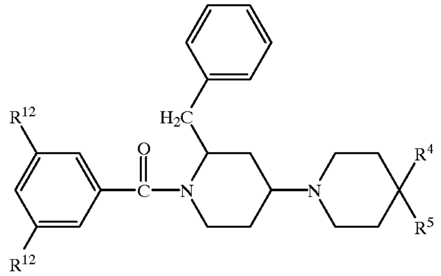
| Co. No. | Ex. No. | $R^{12}$ | $R^4$ | $R^5$ | Physical data |
|---|---|---|---|---|---|
| 69 | B8 | $CH_3$ | $CH_2$—O—$CH_3$ | 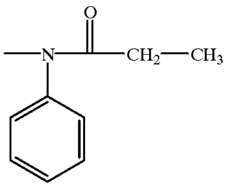 | (±)-cis |
| 70 | B6 | F | phenyl | 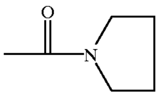 | (±)-cis |
| 71 | B8 | $CH_3$ | $CH_2$—O—$CH_3$ | 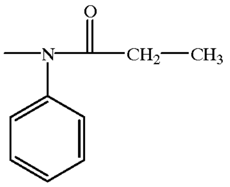 | (±)-cis |
| 72 | B13 | $CF_3$ | H | 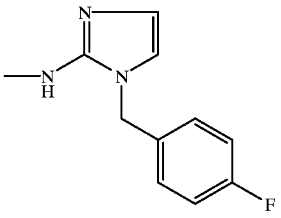 | (±)-cis |
| 73 | B13 | $CF_3$ | H | 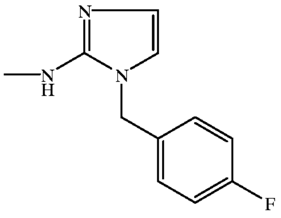 | (±)-trans |
| 74 | B1b | $CF_3$ | OH | 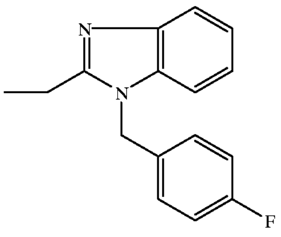 | (±)-cis |

TABLE 1-continued

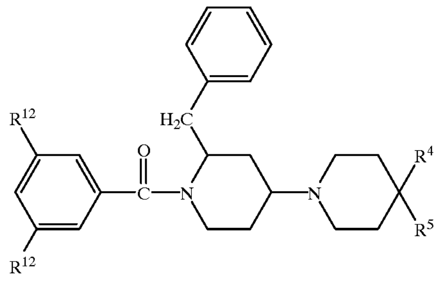

| Co. No. | Ex. No. | $R^{12}$ | $R^4$ | $R^5$ | Physical data |
|---|---|---|---|---|---|
| 75 | B1b | $CF_3$ | OH | 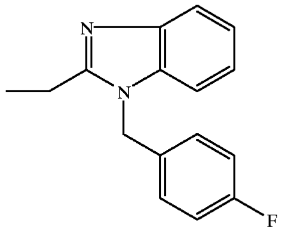 | (±)-trans |
| 76 | B1b | $CF_3$ | phenyl | $-C(=O)-O-C_2H_5$ | (±)-trans |
| 77 | B1b | $CF_3$ | phenyl | $-C(=O)-O-C_2H_5$ | (±)-cis |
| 78 | B1b | $CF_3$ | phenyl | $-NH-C(=O)-CH_3$ | (±)-cis |
| 79 | B1b | $CF_3$ | phenyl | $-NH-C(=O)-CH_3$ | (±)-trans |

TABLE 2

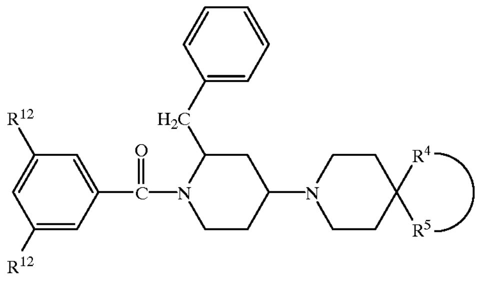

| Co. No. | Ex. No. | $R^{12}$ | $-R^4-R^5-$ | Physical data |
|---|---|---|---|---|
| 56 | B2 | $CH_3$ | $-O-CH_2-CH_2-O-$ | (±)-cis; mp. 65.6° C. |
| 57 | B2 | $CH_3$ | $-O-CH_2-CH_2-O-$ | (±)-trans; mp. 70.8° C. |
| 58 | B1a | $CF_3$ | $-C(=O)-NH-CH_2-N$(phenyl)- | (±)-cis |
| 59 | B1a | $CF_3$ | $-C(=O)-NH-CH_2-N$(phenyl)- | (±)-trans |
| 80 | B1a | $CF_3$ | $-C(=O)-N(CH_3)-CH_2-N$(phenyl)- | (±)-cis |
| 81 | B1a | $CF_3$ | $-C(=O)-N(CH_3)-CH_2-N$(phenyl)- | (±)-trans |

TABLE 3

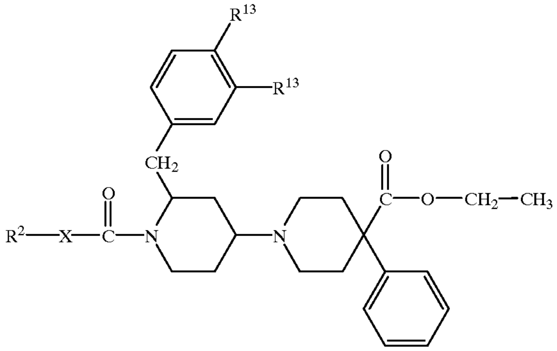

| Co. No. | Ex. No. | $R^{13}$ | X* | $R^2$ | Physical data |
|---|---|---|---|---|---|
| 82 | B12 | H | d.b. | 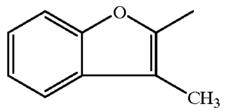 | (±)-trans |
| 83 | B6 | H | d.b. | 3-(trifluoro)phenyl | (±)-cis |
| 84 | B12 | H | d.b. | 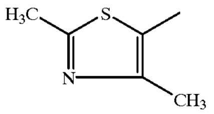 | (±)-trans |
| 85 | B12 | H | d.b. | 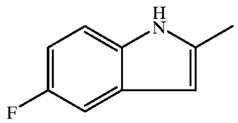 | (±)-cis |
| 86 | B12 | H | d.b. | 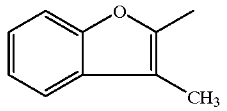 | (±)-cis |
| 87 | B12 | H | d.b. | 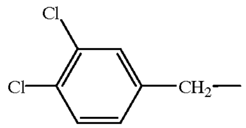 | (±)-cis |
| 88 | B1b | F | d.b. | 3,5-di(trifluoromethyl)phenyl | (±)-cis |
| 89 | B6 | H | d.b. | 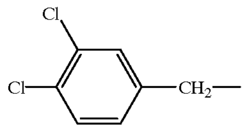 | (±)-trans |
| 90 | B6 | H | d.b. | 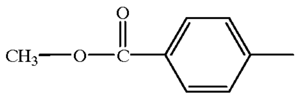 | (±)-trans |
| 91 | B6 | H | d.b. | 3-methylphenyl | (±)-trans |
| 92 | B6 | H | d.b. | 3-cyanophenyl | (±)-trans |
| 93 | B6 | H | d.b. | 2,4,6-trimethylphenyl | (±)-trans |
| 94 | B6 | H | d.b. | 2-naphtalenyl | (±)-trans |
| 95 | B6 | H | d.b. | 2-quinoxalinyl | (±)-trans |
| 96 | B6 | H | d.b. | 2,6-dichloro-4-pyridinyl | (±)-trans |
| 97 | B6 | H | d.b. | 2-furanyl | (±)-trans |
| 98 | B6 | H | d.b. | $(CH_3)_2$—CH— | (±)-trans |

TABLE 3-continued
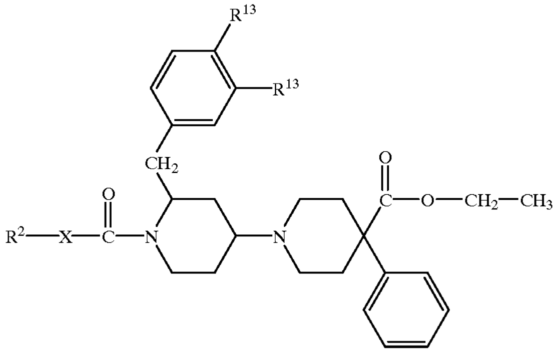
| Co. No. | Ex. No. | $R^{13}$ | X* | $R^2$ | Physical data |
|---|---|---|---|---|---|
| 99 | B6 | H | d.b. | 1-methyl-2-pyrrolyl | (±)-trans |
| 100 | B6 | H | d.b. | 2-furanyl | (±)-cis |
| 101 | B6 | H | d.b. | 2-quinoxalinyl | (±)-cis |
| 102 | B6 | H | d.b. | 2,6-dichloro-4-pyridinyl | (±)-cis |
| 103 | B6 | H | —S— | phenyl | (±)-cis |
*d.b. means direct bond
TABLE 4
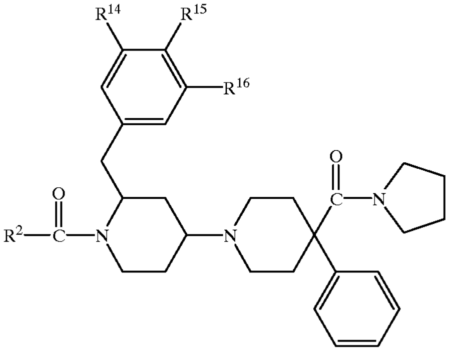
| Co. No. | Ex. No. | $R^{14}$ | $R^{15}$ | $R^{16}$ | $R^2$ | Physical data |
|---|---|---|---|---|---|---|
| 104 | B12 | H | H | H | 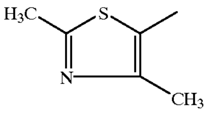 | (±)-cis |
| 105 | B12 | H | H | H | 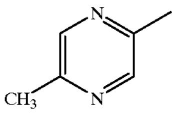 | (±)-cis |
| 106 | B12 | H | H | H | 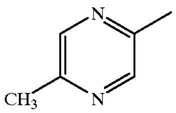 | (±)-trans |
| 107 | B12 | H | H | H | 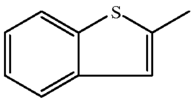 | (±)-trans |

TABLE 4-continued

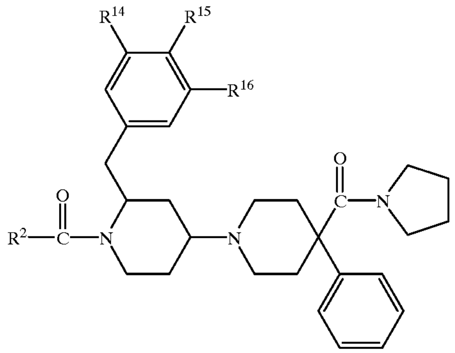

| Co. No. | Ex. No. | $R^{14}$ | $R^{15}$ | $R^{16}$ | $R^2$ | Physical data |
|---|---|---|---|---|---|---|
| 108 | B12 | H | H | H | 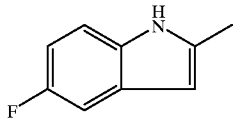 | (±)-trans |
| 109 | B1b | F | H | $CF_3$ | 3,5-di(trifluoromethyl)phenyl | (±)-cis |
| 110 | B1b | F | H | $CF_3$ | 3,5-di(trifluoromethyl)phenyl | (±)-trans |
| 111 | B1c | H | H | $CF_3$ | 3,5-di(trifluoromethyl)phenyl | (±)-cis |
| 112 | B1c | H | H | $CF_3$ | 3,5-di(trifluoromethyl)phenyl | (±)-trans |
| 113 | B1b | H | F | F | 3,5-di(trifluoromethyl)phenyl | (±)-cis |
| 114 | B1b | H | F | F | 3,5-di(trifluoromethyl)phenyl | (±)-trans |
| 115 | B6 | H | Cl | Cl | 3,5-di(trifluoromethyl)phenyl | (±)-cis |
| 116 | B6 | H | Cl | Cl | 3,5-di(trifluoromethyl)phenyl | (±)-trans |
| 117 | B6 | H | H | H | $(CH_3)_2$—CH— | (±)-cis |
| 118 | B6 | H | H | H | 3-(trifluoromethyl)phenyl | (±)-trans |

TABLE 5

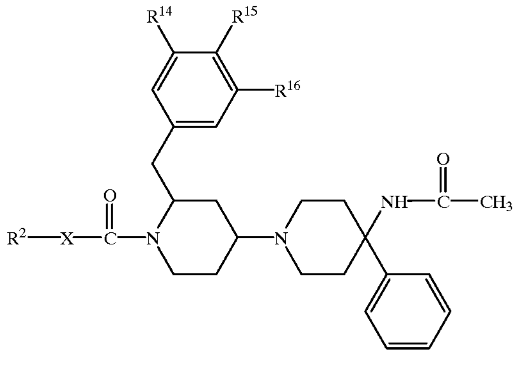

| Co. No. | Ex. No. | $R^{14}$ | $R^{15}$ | $R^{16}$ | X* | $R^2$ | Physical data |
|---|---|---|---|---|---|---|---|
| 119 | B12 | H | H | H | d.b. | 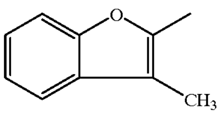 | (±)-cis |
| 120 | B12 | H | H | H | d.b. | 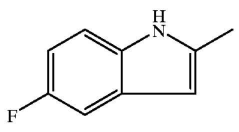 | (±)-cis |

TABLE 5-continued

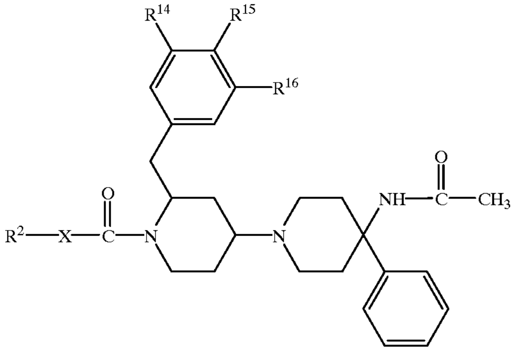

| Co. No. | Ex. No. | $R^{14}$ | $R^{15}$ | $R^{16}$ | X* | $R^2$ | Physical data |
|---|---|---|---|---|---|---|---|
| 121 | B12 | H | H | H | d.b. | 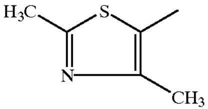 | (±)-trans |
| 122 | B6 | H | H | H | d.b. | 3-cyanophenyl | (±)-trans |
| 123 | B6 | H | H | H | d.b. | 3-methylphenyl | (±)-cis |
| 124 | B1b | F | H | $CF_3$ | d.b. | 3,5-di(trifluoromethyl)phenyl | (±)-cis |
| 125 | B1b | F | H | $CF_3$ | d.b. | 3,5-di(trifluoromethyl)phenyl | (±)-trans |
| 126 | B6 | H | H | H | d.b. | 3-(trifluoromethyl)phenyl | (±)-cis |
| 127 | B14 | H | H | H | d.b. | 3,5-di(trifluoromethyl)phenyl | (±)-cis |
| 128 | B1b | H | F | F | d.b. | 3,5-di(trifluoromethyl)phenyl | (±)-trans |
| 129 | B1b | H | F | F | d.b. | 3,5-di(trifluoromethyl)phenyl | (±)-cis |
| 130 | B6 | H | H | H | d.b. | 2,4,6-trimethylphenyl | (±)-cis |
| 131 | B6 | H | H | H | d.b. | 2,4,6-trimethoxyphenyl | (±)-cis |
| 132 | B6 | H | H | H | d.b. | 4-(trifluoromethoxy)phenyl | (±)-cis |
| 133 | B6 | H | H | H | d.b. | 2-thienyl | (±)-cis |
| 134 | B6 | H | H | H | d.b. | 2-quinolinyl | (±)-cis |
| 135 | B6 | H | H | H | d.b. | 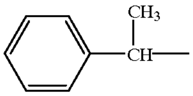 | (±)-cis |
| 136 | B6 | H | H | H | d.b. | 2,4-dichlorophenyl | (±)-trans |
| 137 | B6 | H | H | H | d.b. | 1-methyl-2-pyrrolyl | (±)-trans |
| 138 | B6 | H | H | H | d.b. | 2-naphtalenyl | (±)-trans |
| 139 | B6 | H | H | H | d.b. | 2-quinoxalinyl | (±)-trans |
| 140 | B6 | H | H | H | d.b. | 2-naphtalenyl | (±)-trans |
| 141 | B6 | H | H | H | d.b. | 2-quinoxalinyl | (±)-cis |
| 142 | B6 | H | H | H | d.b. | 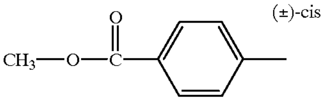 | (±)-cis |
| 143 | B6 | H | H | H | d.b. | 2-furanyl | (±)-cis |
| 144 | B6 | H | H | H | d.b. | 2,6-dichloro-4-pyridinyl | (±)-trans |
| 145 | B6 | H | H | H | d.b. | 2-furanyl | (±)-trans |
| 146 | B6 | H | H | H | d.b. | 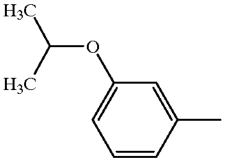 | (±)-cis |
| 147 | B6 | H | H | H | d.b. | 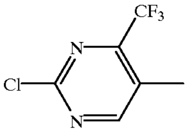 | (±)-cis |

TABLE 5-continued

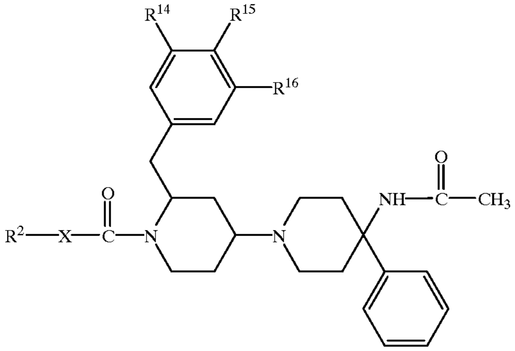

| Co. No. | Ex. No. | $R^{14}$ | $R^{15}$ | $R^{16}$ | X* | $R^2$ | Physical data |
|---|---|---|---|---|---|---|---|
| 148 | B6 | H | H | H | d.b. | 2-naphtalenyl | (±)-cis |
| 149 | B6 | H | H | H | d.b. | 2-benzothienyl | (±)-cis |
| 150 | B6 | H | H | H | d.b. | 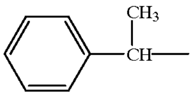 | (±)-cis |
| 151 | B6 | H | H | H | —S— | phenyl | (±)-cis |
| 152 | B6 | H | H | H | d.b. | 1-methyl-2-pyrrolyl | (±)-cis |
| 153 | B1a | H | $CF_3$ | H | d.b. | 3,5-di(trifluoromethyl)phenyl | (±)-cis |
| 154 | B1a | H | $CF_3$ | H | d.b. | 3,5-di(trifluoromethyl)phenyl | (±)-trans |

*d.b. means direct bond

C. Pharmacological Examples

Example C.1

Antagonism of Substance-P Induced Relaxation of the Pig Coronary Arteries

Segments of coronary arteries taken from pigs (killed by injection of an overdose of sodium pentobarbital) were inverted and mounted for recording of isometric tension in organ baths (volume 20 ml) with the endothelium at the outside. The preparations were bathed in Krebs—Henseleit solution. The solution was kept at 37° C. and gassed with a mixture of $O_2/CO_2$ (95/5). After stabilisation of the preparations, prostaglandin $F_{2\alpha}$ ($10^{-5}$ M) was administered to induce a contraction. This was repeated until contractile responses became stable. Then prostaglandin $F_{2\alpha}$ was again administered and substance P ($3\times10^{-10}$ M and $10^{-9}$ M cumulatively) was added. Substance P induced endothelium dependent relaxations. After washing away the agonists, a known concentration of a compound of formula (I) was added. After an incubation period of 30 minutes, prostaglandin $F_{2\alpha}$ ($10^{-5}$ M) and the same concentrations of substance P as described above were again administered in the presence of the compound to be tested. Relaxations caused by substance P were expressed as relaxations under control conditions, and percentage inhibition (% inhibition) of the response to $10^{-9}$ M substance P was taken as a measure of the antagonistic activity of the compound to be tested. The results for the compounds of the present invention at a certain test concentration are listed in table 6

TABLE 6

| Comp. No. | Concentration test compound | % in-hibition | Comp. No. | Concentration test compound | % inhibition |
|---|---|---|---|---|---|
| 1 | $3 \times 10^{-7}$ | 70.7 | 61 | $3 \times 10^{-9}$ | 66.3 |
| 2 | $3 \times 10^{-8}$ | 26.3 | 62 | $3 \times 10^{-10}$ | 23.8 |
| 3 | $3 \times 10^{-8}$ | 23.5 | 65 | $3 \times 10^{-10}$ | 11.6 |
| 4 | $3 \times 10^{-8}$ | 23.5 | 68 | $3 \times 10^{-9}$ | 21.3 |
| 5 | $3 \times 10^{-8}$ | 66.4 | 70 | $3 \times 10^{-9}$ | 7.2 |
| 6 | $3 \times 10^{-8}$ | 70.7 | 71 | $3 \times 10^{-9}$ | 9.1 |
| 7 | $3 \times 10^{-8}$ | 27.8 | 72 | $3 \times 10^{-9}$ | 40.6 |
| 8 | $3 \times 10^{-8}$ | 49.4 | 73 | $3 \times 10^{-9}$ | 51.3 |
| 9 | $3 \times 10^{-8}$ | 70.0 | 74 | $3 \times 10^{-9}$ | 22.6 |
| 10 | $3 \times 10^{-8}$ | 89.2 | 75 | $3 \times 10^{-9}$ | 68.4 |
| 11 | $3 \times 10^{-8}$ | 94.1 | 76 | $3 \times 10^{-9}$ | 71.3 |
| 12 | $3 \times 10^{-8}$ | 6.0 | 77 | $3 \times 10^{-9}$ | 68.2 |
| 13 | $3 \times 10^{-8}$ | 19.4 | 78 | $3 \times 10^{-9}$ | 40.8 |
| 14 | $3 \times 10^{-8}$ | 42.9 | 79 | $3 \times 10^{-9}$ | 19.4 |
| 15 | $3 \times 10^{-8}$ | 69.6 | 80 | $3 \times 10^{-8}$ | 82.9 |
| 17 | $3 \times 10^{-8}$ | 68.3 | 81 | $3 \times 10^{-9}$ | 93.1 |
| 19 | $3 \times 10^{-8}$ | 12.8 | 82 | $3 \times 10^{-9}$ | 12.5 |
| 20 | $3 \times 10^{-8}$ | 22.7 | 83 | $3 \times 10^{-9}$ | 10.0 |
| 21 | $3 \times 10^{-8}$ | 25.3 | 88 | $3 \times 10^{-9}$ | 68.6 |
| 24 | $3 \times 10^{-8}$ | 13.1 | 91 | $3 \times 10^{-9}$ | 17.6 |
| 25 | $3 \times 10^{-8}$ | 28.2 | 92 | $3 \times 10^{-9}$ | 21.0 |
| 26 | $3 \times 10^{-8}$ | 17.6 | 93 | $3 \times 10^{-9}$ | 7.0 |
| 27 | $3 \times 10^{-8}$ | 12.9 | 96 | $3 \times 10^{-9}$ | 18.4 |
| 28 | $3 \times 10^{-8}$ | 36.3 | 98 | $3 \times 10^{-9}$ | 16.7 |
| 29 | $3 \times 10^{-8}$ | 78.4 | 101 | $3 \times 10^{-9}$ | 7.9 |
| 32 | $3 \times 10^{-8}$ | 21.0 | 102 | $3 \times 10^{-9}$ | 12.9 |
| 33 | $3 \times 10^{-8}$ | 51.4 | 103 | $3 \times 10^{-9}$ | 5.8 |
| 34 | $3 \times 10^{-8}$ | 47.7 | 105 | $3 \times 10^{-9}$ | 10.6 |
| 35 | $3 \times 10^{-8}$ | 50.0 | 106 | $3 \times 10^{-9}$ | 18.2 |
| 36 | $3 \times 10^{-8}$ | 57.5 | 107 | $3 \times 10^{-9}$ | 5.1 |
| 37 | $3 \times 10^{-8}$ | 84.9 | 109 | $3 \times 10^{-9}$ | 68.7 |
| 39 | $3 \times 10^{-8}$ | 63.3 | 110 | $3 \times 10^{-10}$ | 57.6 |
| 40 | $3 \times 10^{-8}$ | 79.4 | 111 | $3 \times 10^{-9}$ | 85.7 |

TABLE 6-continued

| Comp. No. | Concentration test compound | % in-hibition | Comp. No. | Concentration test compound | % inhibition |
|---|---|---|---|---|---|
| 41 | $3 \times 10^{-8}$ | 77.6 | 112 | $3 \times 10^{-9}$ | 96.8 |
| 42 | $3 \times 10^{-8}$ | 66.9 | 113 | $3 \times 10^{-9}$ | 89.3 |
| 43 | $3 \times 10^{-9}$ | 93.7 | 114 | $3 \times 10^{-9}$ | 95.3 |
| 44 | $3 \times 10^{-8}$ | 57.8 | 115 | $3 \times 10^{-9}$ | 91.1 |
| 45 | $3 \times 10^{-8}$ | 85.7 | 116 | $3 \times 10^{-10}$ | 93.1 |
| 46 | $3 \times 10^{-8}$ | 67.8 | 117 | $3 \times 10^{-9}$ | 9.4 |
| 47 | $3 \times 10^{-9}$ | 88.4 | 118 | $3 \times 10^{-9}$ | 36.9 |
| 48 | $3 \times 10^{-9}$ | 92.3 | 121 | $3 \times 10^{-9}$ | 6.3 |
| 49 | $3 \times 10^{-8}$ | 78.1 | 124 | $3 \times 10^{-9}$ | 31.2 |
| 50 | $3 \times 10^{-8}$ | 91.0 | 125 | $3 \times 10^{-9}$ | 20.1 |
| 51 | $3 \times 10^{-8}$ | 90.4 | 128 | $3 \times 10^{-9}$ | 16.7 |
| 52 | $3 \times 10^{-9}$ | 86.0 | 129 | $3 \times 10^{-9}$ | 64.9 |
| 53 | $3 \times 10^{-8}$ | 70.3 | 131 | $3 \times 10^{-9}$ | 21.6 |
| 54 | $3 \times 10^{-8}$ | 83.6 | 134 | $3 \times 10^{-9}$ | 32.0 |
| 55 | $3 \times 10^{-8}$ | 79.3 | 138 | $3 \times 10^{-9}$ | 9.1 |
| 56 | $3 \times 10^{-7}$ | 100 | 144 | $3 \times 10^{-9}$ | 16.6 |
| 57 | $3 \times 10^{-7}$ | 43.2 | 148 | $3 \times 10^{-10}$ | 12.6 |
| 58 | $3 \times 10^{-8}$ | 91.7 | 149 | $3 \times 10^{-10}$ | 9.9 |
| 59 | $3 \times 10^{-9}$ | 80.7 | 153 | $3 \times 10^{-9}$ | 43.5 |
| 60 | $3 \times 10^{-9}$ | 72.8 | 154 | $3 \times 10^{-9}$ | 95.7 |

Example C.2

Antagonism of Substance P Induced Plasma Extravasation in Guinea-pigs

Plasma extravasation was induced by injection of substance P (2 mg/kg) in the femoral artery of female guinea-pigs. Evans Blue dye (30 mg/kg) was injected simultaneously. The test compound or solvent was administered 1 hour prior to substance P injection. 10 minutes after challenge, the animals were checked for blue colouring (a direct measure for plasma extravasation) of the nose, the forepaws, and the conjunctiva. 30 minutes after challenge, the animals were sacrificed by $CO_2$ gas inhalation and checked for blue coloring of the trachea and the urinary bladder. Doses which actively inhibit substance P-induced plasma extravasation are defined as thoses doses at which only ⅓ or less of the total surface area of the nose, forepaws, conjunctiva, trachea or urinary bladder are coloured blue by an intensive extravasation. Table 7 lists the lowest active doses (LAD) in mg/kg for the tested compounds.

TABLE 7

| | LAD (in mg/kg) | | | | |
|---|---|---|---|---|---|
| Co. No. | nose | forepaws | conjunctiva | trachea | urinary bladder |
| 128 | 2.5 | 2.5 | 2.5 | 10 | 10 |
| 59 | 2.5 | 2.5 | 2.5 | 10 | 25 |
| 129 | 10 | 10 | 10 | 10 | 10 |
| 78 | 10 | 10 | 10 | 10 | 10 |
| 79 | 10 | 10 | 10 | 10 | 10 |
| 76 | 10 | 10 | 10 | 10 | 10 |
| 112 | 2.5 | 2.5 | 2.5 | 2.5 | 2.5 |
| 116 | 10 | 10 | 10 | 10 | 2.5 |
| 115 | 10 | 10 | 10 | 10 | 10 |
| 60 | 10 | 10 | 10 | 10 | 10 |
| 61 | 10 | 10 | 10 | 10 | 10 |
| 114 | 0.63 | 0.63 | 0.63 | 2.5 | 10 |
| 80 | 10 | 10 | 10 | 10 | 10 |
| 81 | 10 | 10 | 10 | 10 | 10 |
| 43 | 2.5 | 2.5 | 2.5 | 10 | 10 |
| 47 | 2.5 | 2.5 | 10 | 40 | 40 |
| 48 | 2.5 | 2.5 | 2.5 | 10 | 40 |
| 110 | 10 | 10 | 10 | 10 | 10 |
| 88 | >10 | 10 | 10 | 10 | 10 |

D. Composition Examples

"Active ingredient" (A.I.) as used throughout these examples relates to a compound of formula (I) a pharmaceutically acceptable addition salt, a stereochemically isomeric form thereof or a N-oxide form thereof.

Example D.1

Oral Solution

Methyl 4-hydroxybenzoate (9 g) and propyl 4-hydroxybenzoate (1 g) were dissolved in boiling purified water (4 l). In 3 l of this solution were dissolved first 2,3-dihydroxybutanedioic acid (10 g) and thereafter A.I (20 g). The latter solution was combined with the remaining part of the former solution and 1,2,3-propanetriol (12 l) and sorbitol 70% solution (3 l) were added thereto. Sodium saccharin (40 g) were dissolved in water (500 ml) and raspberry (2 ml) and gooseberry essence (2 ml) were added. The latter solution was combined with the former, water was added q.s. to a volume of 20 l providing an oral solution comprising 5 mg of the active ingredient per teaspoonful (5 ml). The resulting solution was filled in suitable containers.

Example D.2

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in water (200 ml). The wet powder mixture was sieved, dried and sieved again. Then there was added microcrystalline cellulose (100 g) and hydrogenated vegetable oil (15 g). The whole was mixed well and compressed into tablets, giving 10.000 tablets, each containing 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (25 ml). Polyethylene glycol (10 g) was molten and dissolved in $CH_2Cl_2$ (75 ml). The latter solution was added to the former and then there were added magnesium octadecanoate (2.5 g), polyvinylpyrrolidone (5 g) and concentrated colour suspension (30 ml) and the whole was homogenated. The tablet cores were coated with the thus obtained mixture in a coating apparatus.

Example D.3

Injectable Solution

Methyl 4-hydroxybenzoate (1.8 g) and propyl 4-hydroxybenzoate (0.2 g) were dissolved in boiling water (500 ml) for injection. After cooling to about 50° C. there were added while stirring lactic acid (4 g), propylene glycol (0.05 g) and the A.I. (4 g). The solution was cooled to RT and supplemented with water for injection q.s. ad 1 l, giving a solution comprising 4 mg/ml of A.I.. The solution was sterilized by filtration and filled in sterile containers.

What is claimed is:

1. A compound of formula (I)

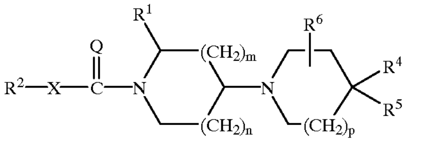

a N-oxide form, a pharmaceutically acceptable addition salt or a stereochemically isomeric form thereof, wherein n is 1;

m is 1;

p is 0 or 2;

=Q is =O or $=NR^3$;

X is a covalent bond or a bivalent radical of formula —O—, —S—, $—NR^3—$;

$R^1$ is $Ar^1$; $Ar^1C_{1-6}$alkyl or di($Ar^1$)$C_{1-6}$alkyl, wherein each $C_{1-6}$alkyl group is optionally substituted with hydroxy, $C_{1-4}$alkyloxy, oxo or a ketalized oxo substituent of formula $—O—CH_2—CH_2—O—$ or $—O—CH_2—CH_2—CH_2—O—$;

$R^2$ is $Ar^2$; $Ar^2C_{1-6}$alkyl; Het or Het$C_{1-6}$alkyl;

$R^3$ is hydrogen or $C_{1-6}$alkyl;

$R^4$ is hydrogen; $C_{1-4}$alkyl; $C_{1-4}$alkyloxy$C_{1-4}$alkyl; hydroxy$C_{1-4}$alkyl; carboxyl; $C_{1-4}$alkyloxycarbonyl or $Ar^3$;

$R^5$ is hydrogen; hydroxy; $Ar^3$; $Ar^3C_{1-6}$alkyloxy; di($Ar^3$)$C_{1-6}$alkyloxy; $Ar^3C_{1-6}$alkylthio; di($Ar^3$)$C_{1-6}$alkylthio; $Ar^3C_{1-6}$alkylsulfoxy; di($Ar^3$)$C_{1-6}$alkylsulfoxy; $Ar^3C_{1-6}$alkylsulfonyl; di($Ar^3$)$C_{1-6}$alkylsulfonyl; $—NR^7R^8$; $C_{1-6}$alkyl substituted with $—NR^7R^8$; or a radical of formula (a-1)

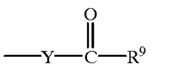

or (a-2)

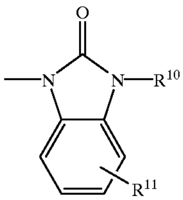

wherein $R^7$ is hydrogen; $C_{1-6}$alkyl; pyridinyl or $Ar^3$;

$R^8$ is hydrogen; $C_{1-6}$alkyl; $Ar^3C_{1-6}$alkyl; di($Ar^3$)$C_{1-6}$alkyl; imidazolyl substituted with $Ar^3$, $C_{1-6}$alkyl or $Ar^3C_{1-6}$alkyl; benzoxazolyl or benzothiazolyl;

$R^9$ is hydrogen; hydroxy; $C_{1-6}$alkyl; $C_{1-6}$alkyloxy; $Ar^3$; $Ar^3C_{1-6}$alkyl; di($Ar^3$)$C_{1-6}$alkyl; amino; mono- or di($C_{1-6}$alkyl)amino; imidazolyl; imidazolyl substituted with $Ar^3$, $C_{1-6}$alkyl or $Ar^3C_{1-6}$alkyl; pyrrolidinyl; piperidinyl; homopiperidinyl; morpholinyl or thiomorpholinyl;

$R^{10}$ is hydrogen or $C_{1-6}$alkylcarbonyl;

$R^{11}$ is hydrogen; halo or mono-, di- or tri(halo)methyl;

Y is $Y^1$ or $Y^2$, wherein $Y^1$ is a covalent bond; $C_{1-6}$alkanediyl; $—NR^7—$ or $—C_{1-6}$alkanediyl-$NR^7—$; or $Y^2$ is —O—, provided that $R^9$ is other than hydroxy or $C_{1-6}$alkyloxy;

$R^4$ and $R^5$ may also be taken together to form a bivalent radical of formula $—O—CH_2—CH_2—O—$ or $—C(=O)—NR^3—CH_2—NR^7—$;

$R^6$ is hydroxy; $C_{1-6}$alkyloxy; $C_{1-6}$alkyl or $Ar^3C_{1-6}$alkyl;

$Ar^1$ is phenyl; phenyl substituted with 1, 2 or 3 substituents each independently selected from halo, $C_{1-4}$alkyl, halo$C_{1-4}$alkyl, cyano, aminocarbonyl, $C_{1-4}$alkyloxy or halo$C_{1-4}$alkyloxy;

$Ar^2$ is naphtalenyl; phenyl; phenyl substituted with 1, 2 or 3 substituents each independently selected from hydroxy, halo, cyano, nitro, amino, mono- or di($C_{1-4}$ alkyl)amino, $C_{1-4}$alkyl, halo$C_{1-4}$alkyl, $C_{1-4}$alkyloxy, halo$C_{1-4}$alkyloxy, carboxyl, $C_{1-4}$alkyloxycarbonyl, aminocarbonyl and mono- or di($C_{1-4}$alkyl) aminocarbonyl;

$Ar^3$ is phenyl or phenyl substituted with 1, 2 or 3 substituents selected from halo, hydroxy, amino, nitro, aminocarbonyl, $C_{1-6}$alkyl, halo$C_{1-6}$alkyl or $C_{1-6}$alkyloxy; and Het is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl or mono-, di- or tri(halo)methyl.

2. A compound as claimed in claim 1 wherein $R^8$ is hydrogen; $C_{1-6}$alkyl; $Ar^3C_{1-6}$alkyl; di($Ar^3$)$C_{1-6}$alkyl; benzoxazolyl or benzothiazolyl; $R^9$ is hydrogen; hydroxy; $C_{1-6}$alkyl; $C_{1-6}$alkyloxy; $Ar^3$; $Ar^3C_{1-6}$alkyl; di($Ar^3$)$C_{1-6}$ alkyl; amino; mono- or di($C_{1-6}$alkyl)amino; pyrrolidinyl; piperidinyl; homo-piperidinyl; morpholinyl or thiomorpholinyl; and Het is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl or mono-, di- or tri(halo)methyl.

3. A compound as claimed in claim 2 wherein $R^1$ is $Ar^1C_{1-6}$alkyl, $R^2$ is phenyl substituted with 2 substituents selected from methyl or trifluoromethyl, X is a covalent bond and =Q is =O.

4. A pharmaceutical composition comprising a pharmaceutically acceptable carrier, and as active ingredient a compound as claimed in claim 1.

5. A process of preparing a pharmaceutical composition comprising mixing a pharmaceutically acceptable carrier with a compound as claimed in claim 1.

6. A method of treating a central nervous system disorder comprising administering to a warm-blooded animal a therapeutically effective amount of a compound of formula (I)

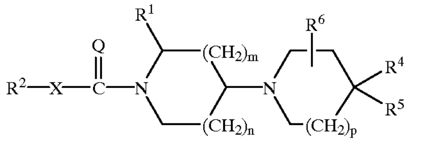

a N-oxide form, a pharmaceutically acceptable addition salt or a stereochemically isomeric form thereof, wherein n is 1;

m is 1;

p is 0, 1 or 2;

=Q is =O or =$NR^3$;

X is a covalent bond or a bivalent radical of formula —O—, —S—, —$NR^3$—;

$R^1$ is $Ar^1$; $Ar^1C_{1-6}$alkyl or di($Ar^1$)$C_{1-6}$alkyl, wherein each $C_{1-6}$alkyl group is optionally substituted with hydroxy, $C_{1-4}$alkyloxy, oxo or a ketalized oxo substituent of formula —O—$CH_2$—$CH_2$—O— or —O—$CH_2$—$CH_2$—$CH_2$—O—;

$R^2$ is $Ar^2$; $Ar^2C_{1-6}$alkyl; Het or Het$C_{1-6}$alkyl;

$R^3$ is hydrogen or $C_{1-6}$alkyl;

$R^4$ is hydrogen; $C_{1-4}$alkyl; $C_{1-4}$alkyloxy$C_{1-4}$alkyl; hydroxy$C_{1-4}$alkyl; carboxyl; $C_{1-4}$alkyloxycarbonyl or $Ar^3$;

$R^5$ is hydrogen; hydroxy; $Ar^3$; $Ar^3C_{1-6}$alkyloxy; di($Ar^3$) $C_{1-6}$alkyloxy; $Ar^3C_{1-6}$alkylthio; di($Ar^3$) $C_{1-6}$alkylthio; $Ar^3C_{1-6}$alkylsulfoxy; di($Ar^3$)$C_{1-6}$alkylsulfoxy; $Ar^3C_{1-6}$ alkylsulfonyl; di($Ar^3$)$C_{1-6}$alkylsulfonyl; —$NR^7R^8$; $C_{1-6}$alkyl substituted with —$NR^7R^8$; or a radical of formula (a-1)

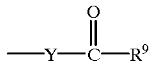

or (a-2)

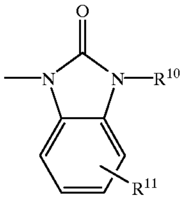

wherein $R^7$ is hydrogen; $C_{1-6}$alkyl; pyridinyl or $Ar^3$;

$R^8$ is hydrogen; $C_{1-6}$alkyl; $Ar^3C_{1-6}$alkyl; di($Ar^3$)$C_{1-6}$ alkyl; imidazolyl substituted with $Ar^3$, $C_{1-6}$alkyl or $Ar^3C_{1-6}$alkyl; benzoxazolyl or benzothiazolyl;

$R^9$ is hydrogen; hydroxy; $C_{1-6}$alkyl; $C_{1-6}$alkyloxy; $Ar^3$; $Ar^3C_{1-6}$alkyl; di($Ar^3$)$C_{1-6}$alkyl; amino; mono- or di($C_{1-6}$alkyl)amino; imidazolyl; imidazolyl substituted with $Ar^3$, $C_{1-6}$alkyl or $Ar^3C_{1-6}$alkyl; pyrrolidinyl; piperidinyl; homopiperidinyl; morpholinyl or thiomorpholinyl;

$R^{10}$ is hydrogen or $C_{1-6}$alkylcarbonyl;

$R^{11}$ is hydrogen; halo or mono-, di- or tri(halo)methyl;

Y is $Y^1$ or $Y^2$, wherein $Y^1$ is a covalent bond; $C_{1-6}$alkanediyl; —$NR^7$— or —$C_{1-6}$alkanediyl-$NR^7$—; or $Y^2$ is —O—, provided that $R^9$ is other than hydroxy or $C_{1-6}$alkyloxy;

$R^4$ and $R^5$ may also be taken together to form a bivalent radical of formula —O—$CH_2$—$CH_2$—O— or —C(=O)—$NR^3$—$CH_2$—$NR^7$—;

$R^6$ is hydroxy; $C_{1-6}$alkyloxy; $C_{1-6}$alkyl or $Ar^3C_{1-6}$alkyl;

$Ar^1$ is phenyl; phenyl substituted with 1, 2 or 3 substituents each independently selected from halo, $C_{1-4}$alkyl, halo$C_{1-4}$alkyl, cyano, aminocarbonyl, $C_{1-4}$alkyloxy or halo$C_{1-4}$alkyloxy;

$Ar^2$ is naphtalenyl; phenyl; phenyl substituted with 1, 2 or 3 substituents each independently selected from hydroxy, halo, cyano, nitro, amino, mono- or di($C_{1-4}$ alkyl)amino, $C_{1-4}$alkyl, halo$C_{1-4}$alkyl, $C_{1-4}$alkyloxy, halo$C_{1-4}$alkyloxy, carboxyl, $C_{1-4}$alkyloxycarbonyl, aminocarbonyl and mono- or di($C_{1-4}$alkyl) aminocarbonyl;

$Ar^3$ is phenyl or phenyl substituted with 1, 2 or 3 substituents selected from halo, hydroxy, amino, nitro, aminocarbonyl, $C_{1-6}$alkyl, halo$C_{1-6}$alkyl or $C_{1-6}$alkyloxy; and Het is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl or mono-, di- or tri(halo)methyl.

7. The method of claim 6, wherein the central nervous system disorder is selected from schizoprenia, mania, dementia, Alzheimer's disease, anxiety, AIDS-related dementia, diabetic neuropathy, multiple sclerosis, depression, Parkinson's disease, drug dependence or substance abuse.

8. The method of claim 7, wherein the disorder is selected from depression or anxiety.

* * * * *